(12) United States Patent
Nomura et al.

(10) Patent No.: US 7,537,906 B2
(45) Date of Patent: May 26, 2009

(54) APOPTOSIS INDUCER AND METHOD OF SCREENING FOR A SUBSTANCE INHIBITING ACYLATED HOMOSERINE LACTONE

(75) Inventors: Nobuhiko Nomura, 104-303, 4-10-3, Azuma, Tsukuba-shi, Ibaraki 305-0031 (JP); Hitoshi Miyazaki, 24-32, Inarimae, Tsukuba-shi, Ibaraki 305-0061 (JP)

(73) Assignees: Nobuhiko Nomura, Ibaraki (JP); Hitoshi Miyazaki, Ibaraki (JP); Nippon Shokubai Co., Ltd., Osaka (JP)

( * ) Notice: Subject to any disclaimer, the term of this patent is extended or adjusted under 35 U.S.C. 154(b) by 814 days.

(21) Appl. No.: 10/765,048

(22) Filed: Jan. 28, 2004

(65) Prior Publication Data

US 2004/0229944 A1 Nov. 18, 2004

(30) Foreign Application Priority Data

Jan. 29, 2003 (JP) ............................ 2003-021047
Jan. 29, 2003 (JP) ............................. 2003-21053

(51) Int. Cl.
C12Q 1/00 (2006.01)
G01N 33/574 (2006.01)

(52) U.S. Cl. ........................................ 435/7.23; 435/4

(58) Field of Classification Search ....................... None
See application file for complete search history.

(56) References Cited

U.S. PATENT DOCUMENTS

| | | | |
|---|---|---|---|
| 5,591,872 A | * | 1/1997 | Pearson et al. ............... 549/321 |
| 2002/0054769 A1 | * | 5/2002 | Nakamura .................... 399/15 |
| 2002/0054869 A1 | * | 5/2002 | Koo et al. ................ 424/94.63 |

FOREIGN PATENT DOCUMENTS

| | | |
|---|---|---|
| JP | 2002-514092 A | 5/2002 |
| WO | WO 98/58075 A2 | 12/1998 |
| WO | WO 01/74801 A1 | 10/2001 |
| WO | WO 03/022828 A1 | 3/2003 |
| WO | WO 03/026641 A2 | 4/2003 |
| WO | WO 03/026641 A3 | 4/2003 |

OTHER PUBLICATIONS

Smith et al. (J. Immunol. 2001; 167; 366-374).*
Zimmerman et al. (Science 1999; 286: 1741-1744).*
Tateda et al. (Infection and Immunity 2003; 71: 5785-5793).*
Smith et al. (J. Immunol. 2001; 167; 366-374, IDS.*
Rajan et al. (Am. J. Respir. Cell Mol. Biol. 2000; 23: 304-312).*
Telford et al. (Infection and Immunity, 1998; 36-42).*
Maianski et al. (Blood, 2002; 101: 1987-1995).*
Carson et al., "Apoptosis and Disease," The Lancet, vol. 341, pp. 1251-1254 (1993).
Ellis et al., "Mechanisms and Functions of Cell Death," *Annu. Rev. Cell Biol.*, vol. 7, pp. 663-698 (1991).
Kerr et al., "Apoptosis: A Basic Biological Phenomenon with Wide-Ranging Implications in Tissue Kinetics," *Br. J. Cancer*, vol. 26, pp. 239-257 (1972).
Saunders, J., "Death in Embryonic Systems," *Science*, vol. 154, pp. 604-612 (1966).
Smith et al., "IL-8 Production in Human Lung Fibroblasts and Epithelial Cells Activated by the *Pesudomonas* Autoinducer N-3-Oxododecanoyl Homoserine Lactone Is Transcriptionally Regulated by NF-*k*B and Activator Protein-2," *The Journal of Immunology*, vol. 167, pp. 366-374 (2001).
Telford et al., "The *Pseudomonas aeruginosa* Quorum-Sensing Signal Molecule N-(3-Oxododecanoyl)-L-Homoserine Lactone Has Immunomodulatory Activity," *Infection and Immunity*, vol. 66, No. 1, pp. 36-42 (1998).
Whiteley et al., "Identification of genes controlled by quorum sensing in *Pseudomonas aeruginosa*," *PNAS*, vol. 96, No. 24, pp. 13904-13909 (1999).
Wyllie et al., "Adrenocortical Cell Deletion: the Role of ACTH," *J. Pathol.*, vol. 111, pp. 85-94 (1973).
Tateda et al. "The *Pseudomonas aeruginosa* Autoinducer N-3-oxododecanoyl Homoserine Lactone Accelerates Apoptosis in Macrophages and Neutrophils," *Infection and Immunity*, vol. 71, No. 10, pp. 5785-5793 (Oct. 2003).
Communication forwarding Partial European Search Report for Application No. 04250486.0 issued Apr. 26, 2004.
Eves et al., "Akt, a Target of Phosphatidylinositol 3-Kinase, Inhibits Apoptosis in a Differentiating Neuronal Cell Line," Molecular and Cellular Biology, 18(4): 2143-2152, 1998.
Jones et al., "Albumin activates the AKT signaling pathway and protects B-chronic lymphocytic leukemia cells from chlorambucil- and radiation-induced apoptosis," Blood, 101(8): 3174-3180, 2003.
Certified translation of Notice of Rejection mailed May 7, 2008 for Japanese Patent Application No. 2003-021053 (6 pages).

* cited by examiner

*Primary Examiner*—Brandon J Fetterolf
(74) *Attorney, Agent, or Firm*—Finnegan, Henderson, Farabow, Garrett & Dunner, L.L.P.

(57) ABSTRACT

The present invention relates to an Akt inhibitor comprising a compound represented by formula I:

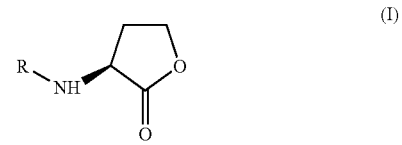

(I)

wherein R is $C_{4-30}$ linear or branched acyl, which may be substituted. The present invention further relates to a method of screening for a substance inhibiting acylated homoserine lactone by culturing animal cells with a test substance in the presence of acylated homoserine lactone represented by the above formula I, and then detecting inhibition of Akt activity or inhibition of the survival signalling pathway in which Akt is involved in the cells.

2 Claims, 19 Drawing Sheets
(1 of 19 Drawing Sheet(s) Filed in Color)

p-ERK, p-p38 and p-Akt represent phospho-ERK, phospho-p38 and phosphor-Akt, respectively.

p-ERK, p-p38 and p-Akt represent phospho-ERK, phospho-p38 and phosphor-Akt, respectively.

M: marker
C: control cas3 and cas9 represent cleaved caspase-3 and cleaved caspase-9 respectively.

US 7,537,906 B2

APOPTOSIS INDUCER AND METHOD OF SCREENING FOR A SUBSTANCE INHIBITING ACYLATED HOMOSERINE LACTONE

BACKGROUND OF THE INVENTION

1. Field of the Invention

The present invention relates to a compound inhibiting Akt, which is a type of kinase, an agent for inducing apoptosis comprising the compound, and a method of inducing apoptosis. The present invention further relates to a method of screening for a substance inhibiting biological activities such as the expression of pathogenesis factors in microorganisms and the generation of biofilms.

2. Description of Related Art

Apoptosis is the process of physiological cell death that has been proposed by Kerr and Wyllie et al., (see Br. J. Cancer 26, 239-257, 1972 and J. Pathol. 111, 85-94, 1973). Apoptosis is not the simple phenomenon of cell disintegration, but is active cell death programmed by the genes of a cell in order to maintain the life of an individual. Apoptosis plays an important role not only in the formation of a body in the developmental process, but also in normal cell turnover, the maintenance of the nervous system, the establishment of the immune system and the like in a mature individual in order to control the cellular society (see Science 154, 605-612, 1966 and Rev. Cell. Biol. 7, 663-698, 1991). Moreover, it has become clear that apoptosis is involved not only in basic life phenomena, but also closely involved in the onset of various diseases, for example cancer, autoimmune diseases, viral infectious diseases such as AIDS and neurodegenerative diseases such as Alzheimer disease (see Lancet 341, 1251-1254, 1993).

Apoptosis is caused by various apoptosis-inducing factors under physiological and pathological conditions, and is defined by morphological changes and biochemical changes characteristic in apoptotic cells. Apoptosis is distinguished from necrosis, which is a passive disintegration process wherein normal cells that have received extreme injuries, such as from burns or bruises, die.

Factors for apoptosis induction include, for example, biological factors such as signals from hormones or cytokines, and removal of growth factors, as well as physical factors such as radioactive rays and heat, and chemical factors such as drugs. The mechanism varies depending on apoptosis-inducing factors. Finally, through a common process mainly comprising DNA fragmentation, cell death occurs.

Apoptosis is a form of physiological cell death essential for normal development and differentiation, and occurs in individual cells, for example during the cell turnover in normal biological tissue. Accordingly, excessive suppression of apoptosis causes many functional disorders.

Specific examples of such disorders resulting from apoptosis suppression include cancer, proliferative dermatosis, chronic rheumatoid arthritis, HIV infection, hepatitis and renal diseases. There are currently no effective therapeutic agents against these disorders, and agents for treating and improving such conditions, which have a high clinical usefulness, have been desired.

In nature, microorganisms must survive under various environments. They are forced to survive under environments that of course include oligotrophy, high or low temperatures and pH changes. In vivo environment, they are forced to survive under the presence of phagocytes or antimicrobial humoral factors (e.g., complements, antibodies and lysozymes). Under such circumstances, bacteria have acquired mechanisms for sensitively sensing changes in the environment where they exist. It has been reported as one of such mechanisms that microorganisms sense their own concentrations in the environment via specific signalling substances, and cleverly control their various biological activities according to the concentrations. Such a cell-to-cell signalling mechanism is referred to as the quorum sensing system.

In this signalling mechanism, a substance called an autoinducer (AI) is involved. Signalling among microorganisms is conducted via the autoinducer, thereby regulating wide-ranging biochemical and physiological functions such as the promotion of gene transcription activity, the expression of pathogenicity and the production of antibiotics. This quorum sensing has been discovered in many gram-negative bacteria. As a typical autoinducer, acylated homoserine lactone has been reported. Furthermore, acylated homoserine lactone has been revealed to be involved in a wide variety of activities of microorganisms. As these activities, production of exoenzymes in *Erwinia carotovora*, which is a plant pathogen, and *Pseudomonas aeruginosa*, which is a causative bacterium of cystic fibrosis, and introduction of Ti plasmid from *Agrobacterium tumefaciens* to a plant are known.

I-gene, R-gene and target genes, are basically responsible for the quarum sensing system. I-gene encodes an AI synthetic enzyme, and R-gene encodes a transcription activation factor (see Marvin Whiteloy et al., Proc. Natl. Acad. Sci., 96, 13904-13909 (1996)). The autoinducer, that is, a group of substances referred to as acylated homoserine lactone, is synthesized by the AI synthetic enzyme. Acylated homoserine lactone is a molecule that can pass through the outer bacterial membrane. Acylated homoserine lactone is diluted and does not exhibit biological activity when a bacterial concentration in an environment is low. However, as bacterial proliferation proceeds and bacterial density in the environment becomes higher, intra- and extrabacterial concentration of acylated homoserine lactone become higher. When the concentration reaches a certain threshold, binding of acylated homoserine lactone with R-gene product (transcriptional activator) is accelerated. This complex binds to the transcriptional regulatory region of target genes to promote the expression of the target genes, as a result, various biologically active substances are expressed.

It has been reported so far that in clinically important bacteria such as bacteria of the genus *Vibrio, Pseudomonas aeruginosa, Serratia* and *Enterobacter*, acylated homoserine lactone promotes the expression of pathogenic factors via the above quorum sensing system. Besides, it has also been shown that acylated homoserine lactone is involved in generation of biofilms by microorganisms (see JP Patent Publication (Kohyo) No. 2002-514092 A).

Biofilms are membranes of organisms, which are generated in an environment with water, particularly on the medial wall surfaces of the duct materials of industrial facilities, the same of domestic piping systems, or the interface on medical transplants, or are generated as lesions of chronic infectious diseases and continue to exist. The biofilm comprises an organic gelatinous structure composed of substrate polymers secreted by resident microorganisms and microorganisms embedded in the structure. The formation of biofilms may limit or completely block the flow in a piping system, or may reduce the lifetime of materials by the corrosive action of embedded bacteria. Control and removal of biofilms from pipe or duct surfaces have been conventionally conducted through the use of corrosive chemical drugs such as chlorine or a strong alkaline solution, or by mechanical means. Such treatments are generally severe for both piping systems and the environment. Microbial resistance against an antimicrobial agent is mainly provided by the protection property of the substrate polymer of a biofilm. In the medical field, the use of high doses of antibiotics has been required for treatment of conditions where biofilms may be involved in. One of the reasons for this is thought to be that the protection ability of biofilm of bacteria is enhanced by extracellular substrate polymers. Therefore, there is a need to control biofilm formation in the medical, environmental and industrial fields.

As described above, the expression of pathogenic factors and biofilm generation are now important issues, so that a method of screening for a substance that inhibits acylated homoserine lactone being involved in these biological activities of microorganisms has been desired. Since acylated homoserine lactone controls various activities in microorganisms, a substance inhibiting acylated homoserine lactone may be screened for by using the survival of microorganisms, or the like as an indicator. However, microorganisms themselves produce acylated homoserine lactone, thus causing bias. This is not preferred as a screening method. Hence, a more effective method of screening for an acylated homoserine lactone-inhibiting substance has been desired.

In the meantime, regarding the effect of an acylated homoserine lactone molecule on animal cells, there have been only a few reports that N-(3-oxododecanoyl)-L-homoserine lactone stimulates IL-8 production in human alveolar cells (see Richard P. Phipps, J. Immunol., 167, 366-374, (2001)) and that the substance promotes TNF-α and IL-12 production in a mouse macrophage culture system (see Gary Telford et al., Infect. Immun., 66, 36-42, (1998)). All of these reports relate to inflammation or immune responses. Both the facts that acylated homoserine lactone inhibits the activities of Akt in animal cells and further induces apoptosis in animal cells have been completely unknown.

SUMMARY OF THE INVENTION

An object of the present invention is to provide an agent for inducing apoptosis useful for prevention and/or treatment of disorders resulting from apoptosis suppression, and a method of screening for a substance inhibiting the biological activities of acylated homoserine lactone.

As a result of intensive studies to achieve the above object, we have discovered that acylated homoserine lactone inhibits the activity of Akt, which is an enzyme essential for cell survival, and effectively induces apoptosis.

Furthermore, we have discovered that a substance inhibiting the biological activity of acylated homoserine lactone can be screened for by culturing animal cells with a test substance in the presence of acylated homoserine lactone, and then detecting inhibition of Akt activity or inhibition of the survival signalling pathway in which Akt is involved in the cells.

That is, the present invention encompasses the following inventions.

(1) A method of inhibiting Akt, comprising using a compound represented by formula I:

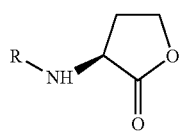

(I)

wherein R is $C_{4-30}$ linear or branched acyl, which may be substituted.

(2) The method of (1), wherein R is $C_{4-30}$ linear or branched acyl having oxo at position 3.

(3) A method of inducing apoptosis in cells, comprising using a compound represented by formula I:

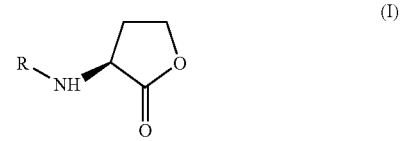

(I)

wherein R is as defined above.

(4) A method of screening for a substance inhibiting acylated homoserine lactone, comprising culturing animal cells with a test substance in the presence of acylated homoserine lactone represented by formula I:

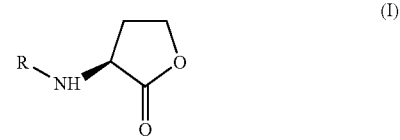

(I)

wherein R is as defined above, and detecting inhibition of Akt activity or inhibition of the survival signalling pathway in which Akt is involved in the cells.

(5) The method of (4), wherein inhibition of the survival signalling pathway in which Akt is involved is detected by detecting apoptosis.

(6) A substance inhibiting acylated homoserine lactone, which is identified by the screening method of (4).

(7) An acylated homoserine lactone inhibitor, which is identified by the screening method of (4).

(8) A kit for using in the screening method of (4), comprising the following elements:

a) an acylated homoserine lactone represented by formula I:

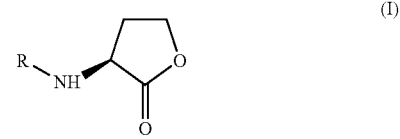

(I)

wherein R is as defined above, b) an animal cell, and c) a means for measuring Akt activity.

(9) A substance inhibiting acylated homoserine lactone, which is identified by the screening method of (5).

(10) An acylated homoserine lactone inhibitor, which is identified by the screening method of (5).

(11) A kit for using in the screening method of (5), comprising the following elements:

a) an acylated homoserine lactone represented by formula I:

$$\underset{R}{\overset{}{\underset{NH}{\diagdown}}}\overset{}{\underset{O}{\diagup}}\overset{O}{\diagdown} \qquad (I)$$

wherein R is as defined above,
b) an animal cell, and
c) a means for measuring Akt activity.

Figure 1:
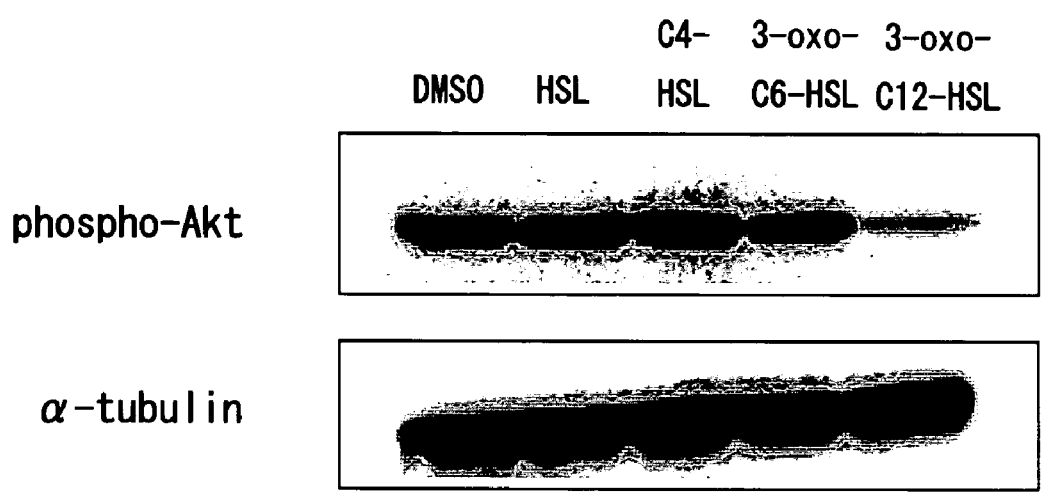
FIG. 1 shows changes in Akt activity in CaCo-2 cells stimulated with DMSO, homoserine lactone hydrochloride, N-butyryl-L-homoserine lactone, N-(3-oxohexanoyl)-L-homoserine lactone and N-(3-oxododecanoyl)-L-homoserine lactone.

The patent or application file contains at least one drawing executed in color. Copies of this patent or patent application publication with color drawings will be provided by the Office upon request and payment of the necessary fee.

DETAILED DESCRIPTION OF THE INVENTION

In the present invention, a compound represented by formula I:

$$\underset{R}{\overset{}{\underset{NH}{\diagdown}}}\overset{}{\underset{O}{\diagup}}\overset{O}{\diagdown} \qquad (I)$$

is referred to as acylated homoserine lactone.

In formula I, R represents $C_{4-30}$, preferably $C_{8-20}$ and more preferably $C_{10-14}$ linear or branched acyl, which may be substituted. Examples of a substituent include hydroxyl, oxo and methyl. Unsubstituted saturated aliphatic acyl and saturated aliphatic acyl having oxo at position 3 are preferred. In addition, a linear form is preferred.

Specific examples of R include, but are not specifically limited to, butyryl, 3-oxobutyryl, 3-hydroxybutyryl, isobutyryl, valeryl, 3-oxovaleryl, isovaleryl, 3-oxoisovaleryl, pivaloyl, hexanoyl, 3-oxohexanoyl, heptanoyl, 3-oxoheptanoyl, octanoyl, 3-oxooctanoyl, nonanoyl, 3-oxononanoyl, decanoyl, 3-oxodecanoyl, undecanoyl, 3-oxoundecanoyl, lauroyl, 3-oxododecanoyl, tridecanoyl, 3-oxotridecanoyl, tetradecanoyl, 3-oxotetradecanoyl, pentadecanoyl, 3-oxopentadecanoyl, palmitoyl, 3-oxopalmitoyl, heptadecanoyl, 3-oxoheptadecanoyl, stearoyl, 3-oxostearoyl, nonadecanoyl, 3-oxononadecanoyl, icosanoyl, 3-oxoicosanoyl, triacontanoyl, 3-oxotriacontanoyl, myristoyl, 3-oxomyristoyl and pyruvoyl.

Specific examples of acylated homoserine lactone represented by formula I include, but are not specifically limited to, N-butyryl-L-homoserine lactone, N-(3-oxobutyryl)-L-homoserine lactone, N-(3-hydroxybutyryl)-L-homoserine lactone, N-isobutyryl-L-homoserine lactone, N-valeryl-L-homoserine lactone, N-(3-oxovaleryl)-L-homoserine lactone, N-isovaleryl-L-homoserine lactone, N-(3-oxoisovaleryl)-L-homoserine lactone, N-pivaloyl-L-homoserine lactone, N-hexanoyl-L-homoserine lactone, N-(3-oxohexanoyl)-L-homoserine lactone, N-heptanoyl-L-homoserine lactone, N-(3-oxoheptanoyl)-L-homoserine lactone, N-octanoyl-L-homoserine lactone, N-(3-oxooctanoyl)-L-homoserine lactone, N-nonanoyl-L-homoserine lactone, N-(3-oxononanoyl)-L-homoserine lactone, N-decanoyl-L-homoserine lactone, N-(3-oxodecanoyl)-L-homoserine lactone, N-undecanoyl-L-homoserine lactone, N-(3-oxoundecanoyl)-L-homoserine lactone, N-lauroyl-L-homoserine lactone, N-(3-oxododecanoyl)-L-homoserine lactone, N-tridecanoyl-L-homoserine lactone, N-(3-oxotridecanoyl)-L-homoserine lactone, N-tetradecanoyl-L-homoserine lactone, N-(3-oxotetradecanoyl)-L-homoserine lactone, N-pentadecanoyl-L-homoserine lactone, N-(3-oxopentadecanoyl)-L-homoserine lactone, N-palmitoyl-L-homoserine lactone, N-(3-oxopalmitoyl)-L-homoserine lactone, N-heptadecanoyl-L-homoserine lactone, N-(3-oxoheptadecanoyl)-L-homoserine lactone, N-stearoyl-L-homoserine lactone, N-(3-oxostearoyl)-L-homoserine lactone, N-nonadecanoyl-L-homoserine lactone, N-(3-oxononadecanoyl)-L-homoserine lactone, N-icosanoyl-L-homoserine lactone, N-(3-oxoicosanoyl)-L-homoserine lactone, N-triacontanoyl-L-homoserine lactone, N-(3-oxotriacontanoyl)-L-homoserine lactone, N-myristoyl-L-homoserine lactone, N-(3-oxomyristoyl)-L-homoserine lactone and N-pyruvoyl-L-homoserine lactone.

In particular, N-(3-oxodecanoyl)-L-homoserine lactone, N-(3-oxoundecanoyl)-L-homoserine lactone, N-(3-oxododecanoyl)-L-homoserine lactone, N-(3-oxotridecanoyl)-L-homoserine lactone and N-(3-oxotetradecanoyl)-L-homoserine lactone are preferred.

The acylated homoserine lactone of the present invention can be synthesized by, for example, forming an amide bond between aliphatic carboxylic acid or the ester thereof and cyclic amino acid. Furthermore, acylated homoserine lactone can be synthesized by a method described in, for example, Chhabra, S. R., P. Stead, N. J. Bainton, G. P. C. Salmond, G. S. A. B. Stewart, P. Williams, and B. W. Bycroft, J. Antibiot., 46, 441-454, 1993, Zhang, L., P. J. Murphy, A. Kerr, and M. E. Tate, Nature, 362, 446-448, 1993, Schaefer A. L., B. L. Hanzelka, A. Eberhard, and E. P. Greenberg, J. Bacteriol., 178, 2897-2901, 1996, and Gao, J. G. and E. A. Meighen. J. Bacteriol., 175, 3856-3862, 1993.

Furthermore, the acylated homoserine lactone of the present invention is biosynthesized by microorganisms, so that it can be separated and purified using a method conventionally employed in the art from the culture product obtained by culturing microorganisms.

First Invention

A first invention of the present application relates to an Akt inhibitor comprising acylated homoserine lactone, an agent for inducing apoptosis comprising the Akt inhibitor, and a method of inducing apoptosis in cells using acylated homoserine lactone.

Acylated homoserine lactone was reacted with various animal cells, and then Akt activity in the cells was determined by the Western blotting method. As a result, we have discovered that specific acylated homoserine lactone effectively inhibits the phosphorylation of Akt.

In the present invention, Akt is serine/threonine kinase, which is activated in the downstream of PI3K (phosphatidylinositide 3-OH kinase), and PI3K-Akt pathway is known as one of the survival signalling pathways. In addition, Akt has also been reported to have activity to inhibit apoptosis in cells (JP Patent Publication (Kohyo) No. 2002-528390 A).

In the present invention, "apoptosis" has a meaning generally used in the art, and specifically refers to cell death, which is actively induced by a cell itself under physiological conditions. The morphology of apoptosis is characterized by chromosome aggregation in cell nuclei, fragmentation of cell nuclei, disappearance of microvilli of cell cortex, and chromatin condensation. Cells shrink, and then are immediately incorporated by surrounding cells such as macrophages without extracellular releasing of cell contents. Thus, apoptosis causes no inflammation and has no effect on surrounding cells. On the other hand, necrosis caused by environmental deterioration greatly differs from apoptosis in that cell contents are released.

Because of the above characteristics, apoptosis in cells can be detected by various methods. Examples of a method for detecting apoptosis include, but are not specifically limited to, a method that involves staining using, for example, DNA binding fluorescent dye such as aminobenzimide (e.g., Hoechst 33342, 33582 and 333258), and then observing chromatin condensation under a fluorescence microscope; a method that involves extracting and separating fragmented DNA by centrifugation or the like, and then quantifying by colorimetry or the like; a method that involves detecting fragmented DNA as "ladder" in agarose gel electrophoresis; and the TUNEL (terminal deoxynucleotidyl transferase-mediated dUTP-biotin nick end labeling) method that involves histochemically detecting fragmented DNA.

Examples of cells into which apoptosis can be induced using the agent for inducing apoptosis of the present invention include, but are not specifically limited to, plant cells and animal cells. Apoptosis can be particularly effectively induced in animal cells.

According to the present invention, it was shown that acylated homoserine lactone effectively inhibits Akt activity in cancer cells. Thus, acylated homoserine lactone can be used as an Akt inhibitor for cancer cells. Furthermore, when acylated homoserine lactone was applied to cancer cells, reduction in viability of the cancer cell, chromatin condensation and the like were observed. Thus it was also shown that the acylated homoserine lactone of the present invention effectively induces apoptosis in cancer cells. Hence, the acylated homoserine lactone of the present invention can be used as an active ingredient of an anticancer agent.

In the present invention, "Akt inhibitor" refers to an agent that inhibits the activation of Akt, that is, the phosphorylation of Akt, and an agent that inactivates activated Akt. Examples of such an agent include an agent inhibiting the activation of Akt in animal cells, an agent inhibiting normal localization of Akt within cells, an agent inhibiting the action of a substance that activates Akt and an agent degrading an Akt-activating substance.

Furthermore, acylated homoserine lactone represented by formula I differs in its Akt-inhibiting activity depending on types of R groups, so that the apoptosis-inducing effect can be regulated by replacing or modifying the R group. In addition, it is considered that by the use of a combination of a plural number of types of acylated homoserine lactone having different R groups, changes in Akt activity can be controlled and the pharmacological effects thereof can be regulated.

Examples of a disease that can be treated using an agent for inducing apoptosis comprising as an active ingredient the acylated homoserine lactone of the present invention include, but are not specifically limited to, diseases caused by the suppression of apoptosis, such as cancer, which is present in tissue selected from the group consisting of the ovary, breast, pancreas, skin, lung, brain, kidney, liver, epipharynx, central nervous system, prostate, large bowel, colon, rectum, uterine cervix and endometrium, and proliferative dermatosis, rheumatoid arthritis, HIV infection, hepatitis and renal disorders. In particular, the agent for inducing apoptosis is appropriately used in treating cancer of the digestive system, such as colon cancer, and cutaneous cancer.

In the agent for inducing apoptosis of the present invention, acylated homoserine lactone may be a hydrate. Furthermore, acylated homoserine lactone according to the present invention may be in a free form, or a pharmacologically acceptable salt thereof. When a salt is used, specific examples of a salt include an addition salt of alkaline metal, an addition salt of alkaline earth metal, an ammonium salt and an addition salt of amine. However, acylated homoserine lactone in a free form is more preferred.

Next, examples of a dosage form of the acylated homoserine lactone of the present invention include oral preparations such as powder, fine grain agents, granules, tablets, coated tablets and capsules, external preparations such as ointments and patches, suppositories and preparations for injection. Upon formulation, the preparation can be produced using a conventional carrier for formulation by a standard method.

Specifically, when an oral preparation is produced, the acylated homoserine lactone and an excipient, and if necessary an antioxidant, a binder, a disintegrating agent, a lubricant, a coloring agent, a flavoring agent or the like is added, and then the mixture is formulated into powder, a fine grain agent, a granule, a tablet, a coated tablet, a capsule or the like by a standard method.

Examples of an excipient that is used herein include lactose, corn starch, sucrose, glucose, mannitol, sorbit, cyrstalline cellulose and silicon dioxide. Examples of a binder that is used herein include polyvinyl alcohol, polyvinyl ether, methyl cellulose, ethyl cellulose, gum arabic, gum tragacanth, gelatine, shellac, hydroxypropylmethylcellulose, hydroxypropylcellulose, polyvinylpyrrolidone, polypropyleneglycol-polyoxyethylene-block polymer and meglumine. Examples of a disintegrating agent that is used herein include starch, agar, gelatine powder, crystalline cellulose, calcium carbonate, sodium bicarbonate, calcium citrate, dextrin, pectin and carboxymethyl cellulose-calcium. Examples of a lubricant that is used herein include talc, polyethylene glycol, silica and hardened vegetable oil. Examples of a coloring agent that is used herein include coloring agents that are capable of being added to pharmaceuticals. Examples of a flavoring agent that is used herein include cocoa powder, menthol, aroma powder, mentha oil, borneol and cinnamon powder. These tablets and granules may be sugar-coated, or may be appropriately coated with other substances if necessary.

When a preparation for injection is produced, a pH modifier, a resolvent and an isotonizing agent, as well as, if necessary, a solubilizer, a stablizer, an antioxidant or the like are added to the acylated homoserine lactone, thereby formulating it by a standard method.

A method for producing an external preparation is not limited, and it can be produced by a standard method. Specifically, as a material for a base to be used upon formulation, various materials that are generally used for pharmaceuticals, quasi-drugs, cosmetics and the like can be used.

Specific examples of a material for a base to be used herein include animal and vegetable oils, mineral oil, ester oil, waxes, higher alcohols, fatty acids, silicone oil, surfactants, alcohols, polyalcohols, water-soluble polymers, clay minerals and purified water. Furthermore, if necessary, a pH modifier, an antioxidant, a chelating agent, an antiseptic and antifungal agent, a coloring agent, an odorant or the like can be added. However, the materials for the base used in the external preparation of the present invention are not limited thereto. Furthermore, if necessary, a constituent such as a blood stream accelerator, an antimicrobial agent, an anti-inflammatory agent, a cell activator, vitamins, amino acids, a moisturizing agent, a keratolytic agent or the like can be incorporated. In addition, the above material for the base is added in an amount suitable to achieve a concentration that is generally defined for the production of an external preparation.

The clinical dose of acylated homoserine lactone, which is an active ingredient of the agent for inducing apoptosis of the present invention, differs depending on animals, to which the inducer is administered, symptom, seriousness, age, body weight, complication and the like. It also differs depending on salt types and routes of administration. Generally, the clinical dose for an adult per day is between 1 μg and 1 g, preferably between 10 μg and 200 mg, and more preferably between 20 μg and 20 mg.

A target, to which the agent for inducing apoptosis of the present invention is to be administered, is not specifically limited, as long as it is an animal. Examples of such animals include mammals such as horses, dogs, mice, guinea pigs and rats. In particular, the inducer is preferably used for a human.

2nd Invention

A second invention of the present application is based on the finding that acylated homoserine lactone inhibits Akt activity in animal cells, and relates to a method of screening for a substance inhibiting biological activities such as the expression of pathogenesis factors and the generation of biofilms by microorganisms.

Accordingly, in an embodiment of the present invention, screening for a substance inhibiting acylated homoserine lactone is carried out by culturing animal cells with a test substance in the presence of acylated homoserine lactone, and detecting inhibition of Akt activity in the cells. Specifically, when animal cells are cultured with a test substance in the presence of acylated homoserine lactone, the Akt-activity-inhibiting effect of acylated homoserine lactone, which is observed in the case of culture without the test substance, would not be observed or would be observed to decrease, and the test substance can be identified to be a substance inhibiting acylated homoserine lactone.

Akt activity can be detected using a method generally employed in the art, such as the Western blot using an anti-phospho-Akt antibody, that is, an anti-activated Akt antibody (for example, see Baumann C A et al., Nature, 407, 202-207, (2000); Holland E C et al., Nat. Genet., 25, 55-57, (2000)). This antibody has high reactivity and specificity against phospho-Akt, which is an antigen. By the use of this antibody, phospho-Akt can be extremely effectively detected.

Akt is activated in the downstream of PI3K (phosphatidylinositide 3-OH kinase), and plays an important role in the survival signalling pathway. The survival and death of cells are controlled by competition between apoptosis signalling and survival signalling. It has been reported that Akt becomes into an activated form by phosphorylation, and the activated Akt inhibits apoptosis in cells (see JP Patent Publication (Kohyo) No. 2002-528390 A).

It is known that activated Akt promotes cell survival via various substrates (Experimental Medicine Vol 19, No. 13 (extra issue), p. 116, 2001, YODOSHA). Moreover, it becomes clear that the survival-promoting mechanism mediated by Akt comprises 1) a pathway that suppresses apoptosis induction ability by directly phosphorylating molecules involved in apoptosis induction, and 2) a pathway that promote survival by regulating the transcription of apoptosis-promoting molecules or apoptosis-suppressing molecules using transcriptional factors as direct or indirect targets. Since Akt inhibits apoptosis via various substrates, inhibition of Akt activity has an effect on other molecules that are responsible for the survival signalling pathway in which Akt is involved, and finally causes apoptosis in cells.

Hence, in another embodiment of the present invention, screening for a substance inhibiting acylated homoserine lactone can also be carried out by culturing animal cells with a test substance in the presence of acylated homoserine lactone, and detecting inhibition of the survival signalling pathway in which Akt is involved. The detection of inhibition of the survival signalling pathway in which Akt is involved can be carried out by detecting molecules involved in this pathway, the activities and the structures thereof, or their binding with other molecules and the like. Examples of molecules involved in the survival signalling pathway in which Akt is involved are not specifically limited as long as they are somewhat affected by the inhibition of Akt activity, and include, for example, caspase, Bad, Forkhead trascription factor and GSK-3.

Caspase is a member of a group of cysteine protease family that plays a critical role in the induction, determination and execution of apoptosis.

When an inactive precursor of caspase is activated by limited degradation, a protease cascade is formed within cells and the signalling for apoptosis is carried out. That is, caspase activation results in apoptosis. Accordingly, caspase activation refers to the inhibition of the survival signalling pathway in which Akt is involved. Specifically, when animal cells are cultured with a test substance in the presence of acylated homoserine lactone, a caspase-activating effect of acylated homoserine lactone, which is observed in the case of cultures without any test substance, would not be observed or would be observed to decrease, and the test substance can be identified as a substance inhibiting acylated homoserine lactone.

Among caspases, caspase-3 possesses the highest enzyme activity, and executes apoptosis using as substrates various proteins constituting cells, in addition to DNA fragmentation factors. Caspase-9 is activated when mitochondria having received damage caused by apoptosis induction stimuli releases cytochrome c so as to promote the multimerization of Apaf-1 cytochrome c-pro caspase-9. It has also been reported that caspase-9 is directly phosphorylated by Akt, so that the activation of caspase-9 is inhibited. Caspase activity can be measured by a method generally employed in the art, for example, by Western blot.

In addition, among MAP kinase super family members, JNK and p38 have been shown to be activated by various physicochemical stresses inducing apoptosis, suggesting the involvement of MAP kinase in apoptosis. MAP kinase is a member of a group of serine-threonine kinases, which is activated by phosphorylation of both amino acid residues of a threonine residue and a tyrosine residue when cells are stimulated with external stimuli such as a cell growth factor, and is universally present in eukaryotes from yeast to higher animals. This enzyme is a protein kinase molecule comprising monomeric catalytic subunits. The amino acid sequence is highly conserved evolutionarily, and is responsible for a part of the central role of intracellular signalling pathway that controls cell growth and molecules. We have discovered that acylated homoserine lactone promotes the activation, that is, the phosphorylation, of MAP kinase. Therefore, in an embodiment of the present invention, screening for a substance inhibiting acylated homoserine lactone can also be carried out by culturing animal cells with a test substance in the presence of acylated homoserine lactone, and then measuring the activity of MAP kinase in the cells. In the present invention, among MAP kinase super family members, activities of ERK, p38 and JNK are preferably detected. MAP kinase activity can be detected by, for example, measuring activated MAP kinase (phosphorylated MAP kinase (phospho MAP)) by Western blot or the like, similarly to the method employed for detecting Akt activity. Specifically, when animal cells are cultured with a test substance in the presence of acylated homoserine lactone, a MAP kinase-activating effect of acylated homoserine lactone, which is observed in the case of culture without any test substance, would not be observed or would be observed to decrease, and the test substance can be identified as a substance inhibiting acylated homoserine lactone.

Since the inhibition of Akt activity finally causes apoptosis, the present invention also encompasses the detection of apoptosis in "the detection of the inhibition of the survival signalling pathway in which Akt is involved." "Apoptosis" herein has a meaning similar to that described for the above first invention.

Apoptosis in animal cells can be detected by a method generally employed in the art, and the method is not specifically limited. For example, a method similar to that described for the above first invention can be employed.

In the present invention, a substance inhibiting acylated homoserine lactone refers to any of a substance inhibiting the action of acylated homoserine lactone on various cells, in particular, animal cells and microorganisms, an antagonist for the action, a substance inhibiting the secretion of acylated homoserine lactone, and a substance degrading acylated homoserine lactone. Examples of the action of acylated homoserine lactone on various cells are not specifically limited, and include an action to inhibit Akt activity, an action to induce apoptosis, an action inducing the expression of a phatogenic factor by cells, and an action inducing the generation of biofilms by microorganisms.

The present invention is also characterized in that it uses animal cells in screening for a substance inhibiting acylated homoserine lactone. When a substance inhibiting acylated homoserine lactone is screened for by using microorganisms such as bacteria, the result is biased because bacteria themselves produce acylated homoserine lactone. However, since animal cells do not produce acylated homoserine lactone, highly reliable screening can be carried out. Animal cells that can be used in the present invention are not specifically limited. For example, cells derived from mammals and birds can be used, and cells derived from mammals, in particular, humans are preferably used. Furthermore, epithelial tissue, and in particular, cells derived from the epithelial tissue of intestinal mucosa (e.g., CaCo-2: human colon carcinoma cells); endothelial cells, in particular, vascular endothelial cells (e.g., PEC: endothelial cells derived from porcine thoracic aorta); and fibroblasts (e.g., NIH3T3: mouse embryonic fibroblasts) are preferably used. Moreover, on the epithelial layer of intestinal mucosa covering the gut associated lymphatic tissue (GALT) such as Peyer's patch, specially-differentiated mucosal epithelial cells that are referred to as M cells are scattered. These mucosal epithelial cells play an important role in regulating immune response locally in the bowel and in the whole body by actively taking dietary antigens or enterobacteria and providing them to the immune tissue. Hence, the intestinal epithelium is a place where contact with substances produced by microorganisms is expected to take place. Examination of the direct action of acylated homoserine lactone using cells derived from the epithelial tissue of the intestinal mucosa enables to understand the action as a phenomenon that can actually occur in vivo in animals. In addition, among animal cells, cancer cells are preferably used.

In the screening method of the present invention, stimulation with acylated homoserine lactone is carried out by culturing animal cells with a test substance in the presence of acylated homoserine lactone. Culture time for stimulation depends on the concentration of acylated homoserine lactone, the detection method used and types of animal cells employed, and is, generally, between approximately 2 minutes and 72 hours.

In the embodiment wherein screening is carried out by measuring Akt activity, it was shown that when animal cells were cultured in the presence of acylated homoserine lactone, Akt activity decreased for several hours after the start of culture, and then returned to the base level (see Example 1(3) and Example 2(3)). Therefore, in the screening method of the present invention, it is preferred that as a control, animal cells are previously cultured with acylated homoserine lactone in the absence of a test substance; culture time, during which activated Akt shows a decrease, is measured; and then within this time range, animal cells are cultured with acylated homoserine lactone in the presence of the test substance. The culture time in this case also depends on the concentration of acylated homoserine lactone and the types of animal cells used, and is generally between approximately 2 minutes and 2 hours.

Also in the embodiment wherein screening is carried out by measuring caspase activity, it was shown that when animal cells were cultured in the presence of acylated homoserine lactone, caspase activity increased for several hours after the start of culture, and then returned to the base level (see Example 6). Hence, similarly, it is also preferred for this case that as a control, animal cells be previously cultured with acylated homoserine lactone in the absence of a test substance, and then the culture time, during which activated caspase shows a decrease, be measured. Culture time in this case depends also on the concentration of acylated homoserine lactone and types of animal cells employed. The culture time is generally between approximately 1 and 8 hours.

Similarly, in the case of activating MAP kinase by acylated homoserine lactone, when culture is carried out in the presence of acylated homoserine lactone, MAP kinase is activated once and the activity returns to the base level with time. The culture time in this case also depends on the concentration of acylated homoserine lactone and types of animal cells used, and is generally between approximately 2 minutes and 6 hours.

Culture time in the case of screening by detecting apoptosis is generally between approximately 6 and 72 hours.

In the screening method of the present invention, the concentration of acylated homoserine lactone to co-exist with a test substance is generally between 1 and 500 μM, preferably between 20 and 200 μM, and more preferably between 30 and 100 μM.

More specifically, when screening for a substance inhibiting acylated homoserine lactone is carried out using the epithelial cells of human-derived intestinal mucosa and Akt activity as an indicator, it is considered preferable to culture animal cells with a test substance in the presence of 10 μM or more, preferably 30 to 200 μM of acylated homoserine lactone, for approximately 2 minutes to 2 hours, preferably for approximately 2 to 60 minutes. Furthermore, when the inhibition of Akt activity, which should naturally be observed within the range of this culture time, is not observed, or the inhibition of Akt activity decreases, the test substance can be identified to be a substance inhibiting acylated homoserine lactone.

When screening for a substance inhibiting acylated homoserine lactone is carried out using the epithelial cells of human-derived intestinal mucosa, and ERK activity as an indicator, it is considered preferable to culture animal cells with a test substance in the presence of 10 μM or more, preferably 30 to 200 μM, acylated homoserine lactone, for approximately 2 to 30 minutes, and preferably for approximately 5 to 15 minutes. When screening for a substance inhibiting acylated homoserine lactone is carried out using the epithelial cells of human-derived intestinal mucosa, and p38 activity as an indicator, it is considered preferable to culture animal cells with a test substance in the presence of 10 μM or more, preferably 30 to 200 μM of acylated homoserine lactone, for approximately 5 minutes to 6 hours, preferably for approximately 5 to 60 minutes.

In the screening method of the present invention, media that are generally used for culturing animal cells can be used, and are not specifically limited. Examples of such a medium include DMEM media and BME media. As other culture conditions, conditions that are generally used for culturing animal cells can be used.

In the present invention, after animal cells are cultured for the above period of time, reaction is stopped by, for example, rapidly cooling culture cells. Subsequently, Akt activity, caspase activity, apoptosis and the like in the animal cells are detected by the above-described methods. To immediately stop a reaction, the solvent may be removed.

Examples of a sample that may contain a test substance to be screened for according to the present invention are not specifically limited, and include animals (including microorganisms such as molds and Actinomycetes), plant extracts and artificial synthetic substances.

The present invention also relates to a substance inhibiting acylated homoserine lactone that is identified by the above-described screening method. Examples of such a substance are not specifically limited, and include both natural and synthetic substances. The substance inhibiting acylated homoserine lactone of the present invention can be used independently, or be used as an antimicrobial agent together with a conventional antimicrobial agent. The substance inhibiting acylated homoserine lactone of the present invention can inhibit generation of biofilm, so that it is advantageous in that the substance can have an enhanced antimicrobial action against bacteria that have acquired drug resistance. Examples of a known antimicrobial agent that can be used with the substance inhibiting acylated homoserine lactone of the present invention are not specifically limited, and include penicillin (penam)-based antibiotics, cephalosporin (cephem)-based antibiotics, oxacephem-based antibiotics, penem-based antibiotics, carbapenem-based antibiotics, monobactam-based antibiotics, aminoglycoside-based antibiotics, macrolide-based antibiotics, chloramphenicol-based antibiotics, tetracycline-based antibiotics, glycopeptide-based antibiotics, phosphomycin-based antibiotics, lincomycin-based antibiotics, sulfa drugs, para-aminosalicylic acid preparations, isonicotinic acid hydrazide preparations and quinolone-based synthetic antimicrobial agents.

An acylated homoserine lactone inhibitor that is screened for by the method of the present invention can be used as a biofilm inhibitor and as filter- and pipe-clogging inhibitors. Furthermore, since the acylated homoserine lactone inhibitor of the present invention inhibits the expression of pathogenic factors in microorganisms, it can also be used as a therapeutic agent against infectious diseases.

The present invention also relates to a kit for using in the above-described screening method. This kit contains, for example, acylated homoserine lactone represented by formula I, animal cells and a means for measuring Akt activity in the animal cells. Examples of a means for measuring Akt activity include an anti-phospho-Akt antibody and a labeled secondary antibody against the antibody. As a labeled secondary antibody, an antibody that is generally used in the art, for example, an HRP-labeled anti-rabbit IgG antibody, an HRP-labeled anti-mouse IgG antibody or the like can be used.

According to the present invention, apoptosis can be effectively induced in cells, and a useful means is provided for prevention and/or treatment against disorders resulting from apoptosis suppression.

By the screening method of the present invention, a substance inhibiting the effect of acylated homoserine lactone on various cells and a substance inhibiting generation of biofilm by microorganisms can be screened for. Moreover, when the identified substance inhibiting acylated homoserine lactone is used simultaneously with a conventional antimicrobial agent, biofilm generation is inhibited, so that the effect of the antimicrobial agent can be enhanced from several to dozens of times. Hence, the antimicrobial effect against bacteria having drug resistance can be enhanced. Furthermore, with this enhanced antimicrobial effect, intractable infectious diseases can also be effectively treated. Furthermore, the expression of pathogenic factors by microorganisms can also be inhibited by the acylated homoserine lactone inhibitor, so that a strong therapeutic effect can be expected. Also in industrial application, clogging of filter pipes can be prevented with the acylated homoserine lactone inhibitor screened for by the method of the present invention.

This specification includes part or all of the contents as disclosed in the specifications and/or drawings of Japanese Patent Application Nos. 2003-021047 and 2003-021053, which are priority documents of the present application.

DETAILED DESCRIPTION OF THE PREFERRED EMBODIMENTS

Examples of the present invention will be shown below, but the present invention is not specifically limited by these examples.

In the following examples, experimental materials described below were used, unless otherwise specified.

Dulbecco's Modified Eagle Medium (DMEM), fetal calf serum (FCS), non essential amino acid (NEAA) and penicillin/streptomycin (P/S) were purchased from SIGMA and used for cell culture. Dimethyl sulfoxide (DMSO) of Wako Pure Chemical Industries, Ltd was used as a solvent for N-acyl-L-homoserine lactone (AHL). PD98059 and SB203580, the kinase inhibitors, were purchased from CALBIOCHEM. For protein quantification, BCA Protein Assay Reagent (PIERCE) was used. Antibodies used herein were those of the following companies. An anti-phospho-p44/42 MAP kinase antibody, an anti-phospho-p38 MAP kinase antibody, an anti-phospho-SAPK/JNK antibody, an anti-phospho-Akt (Ser473) antibody, an anti-cleaved caspase-3 antibody, an anti-cleaved caspase-9 (D330) antibody, an anti-cleaved PARP (D214) antibody, and an HRP-labeled anti-rabbit IgG antibody were from Cell Signaling. A c-Myc mouse monoclonal antibody and an HRP-labeled anti-mouse IgG antibody were from SANTA CRUZ BIOTECHNOLOGY. An anti-α-tubulin antibody (Ab-1) was from CALBIOCHEM.

EXAMPLE 1

Analysis of Akt Activity by Western Blot (1) Changes in Akt Activity in CaCo-2 Cells by Stimulation with Acylated homoserine lactone CaCo-2, the carcinoma cell line of human colon cancer, was purchased from American Type Culture Collection (ATCC), and cultured at 37° C. in the presence of 5% $CO_2$ using a DMEM medium containing 10% FCS, 1% NEAA, and 1% P/S (100 units/ml penicillin and 100 µg/ml streptomycin).

$6 \times 10^5$ CaCo-2 cells were inoculated per dish using 6 cm dishes (NUNC), washed twice with phosphate buffered saline (PBS) (-), and then cultured for 24 hours in a serum-free DMEM medium containing 1% NEAA. Subsequently, at a final concentration of 100 µM, homoserine lactone hydrochloride, N-butyryl-L-homoserine lactone, N-(3-oxohexanoyl)-L-homoserine lactone and N-(3-oxododecanoyl)-L-homoserine lactone were each added, and then each solution was allowed to react for 10 minutes. In addition, purified acylated homoserine lactone that was used herein had been dissolved in DMSO in a concentration 400 times higher than the target final concentration, and then subjected to filter sterilization (φ 0.22 µm). DMSO at a final concentration of 0.25% was used as a control. In addition, α-tubulin was used as an internal standard.

After reaction, the product was washed twice with cold PBS (-), and then frozen at –80° C. The cells were thawed on ice, 200 µl of a lysis buffer (50 mM HEPES, pH7.5, 50 mM NaCl, 1 mM EDTA, 1.5 mM $MgCl_2$, 1% Triton X-100, 10% glycerine, 10 mM sodium pyrophosphate, 1 mM $Na_3VO_4$, 100 mM NaF, 1 mM PMSF, 10 µg/ml aprotinin and 10 µg/ml leupeptin) was added, and then the cells were scraped off using a scraper. The cells were allowed to stand on ice for 20 minutes, and then centrifuged at 14,000 rpm at 4° C. for 15 minutes, thereby collecting the supernatant. Concentration of the collected protein was measured, and protein equivalent to 50 µg was subjected to SDS-PAGE. After electrophoresis, the product was blotted on a PVDF membrane. When phospho-Akt was measured, blocking was carried out with 5% skim milk/Tris-buffered saline containing 0.1% Tween 20 (TBS-T), and the anti-phospho-Akt (Ser437) antibody and the HRP-labeled anti-rabbit IgG antibody were used as a primary antibody and a secondary antibody, respectively. For α-tubulin used as an internal standard, blocking was carried out with 5% bovine serum albumin (BSA)/TBS-T, and the anti-α-tubulin (Ab-1) and the HRP-labeled anti-mouse IgG antibody were used as a primary antibody and a secondary antibody, respectively. For band detection, Renaissance™ Western Blot Chemiluminescence 255861 Reagent Plus (NEN) or Western Blotting Luminol Reagent (SANTA CRUZ BIOTECHNOLOGY) was used. FIG. 1 shows the results. In addition in the figure that is described below, HSL means homoserine lactone hydrochloride, C4-HSL means N-butyryl-L-homoserine lactone, 3-oxo-C6-HSL means N-(3-oxohexanoyl)-L-homoserine lactone, and 3-oxo-C12-HSL means N-(3-oxododecanoyl)-L-homoserine lactone.

In CaCo-2 cells, Akt is normally in a phosphorylated (activated) form. However, the level of phosphorylated Akt significantly decreased only when N-(3-oxododecanoyl)-L-homoserine lactone was added. Specifically, it was shown that N-(3-oxododecanoyl)-L-homoserine lactone inhibits the activity of Akt.

(2) N-(3-oxododecanoyl)-L-homoserine lactone Concentration-dependent Changes in Akt Activity in CaCo-2 Cells After cell culture, N-(3-oxododecanoyl)-L-homoserine lactones with final concentrations of 0 µM (0.25% DMSO), 1 µM, 10 µM, 30 µM and 100 µM were each added. Akt activity was analyzed by Western blot in a manner similar to that used in (1), except for carrying out reaction for 10 minutes (FIG. 2).

Figure 2:
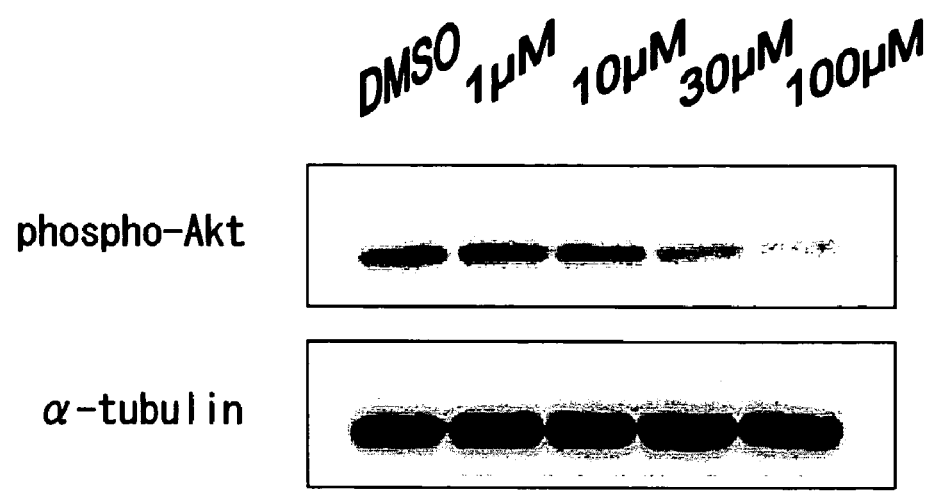
FIG. 2 shows N-(3-oxododecanoyl)-L-homoserine lactone concentration-dependent changes in Akt activity in CaCo-2 cells.
Figure 3:
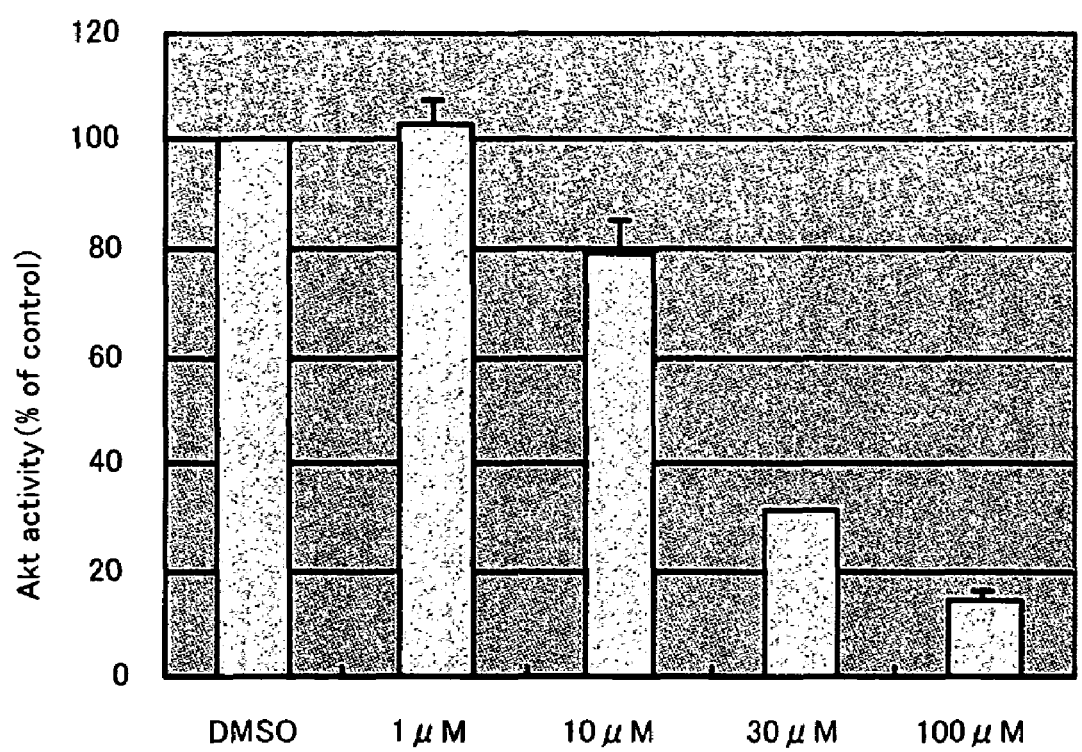
FIG. 3 shows the results of quantifying the band intensities of phospho-Akt in FIG. 2 by LAS-1000 and converting the results into numerical data.

FIG. 3 shows the results of quantifying the band intensities in FIG. 2 by LAS-1000 and converting the results into numerical data. At concentrations of 10 μM or more, the levels of phosphorylated Akt significantly decreased. At 10 μM, 30 μM and 100 μM, Akt activity decreased to 79%, 31% and 14%, respectively, of that in a case where no stimulation was provided.

From the above results, it was shown that in CaCo-2 cells, Akt activity is significantly inhibited by 10 μM or more acylated homoserine lactones.

Figure 4:
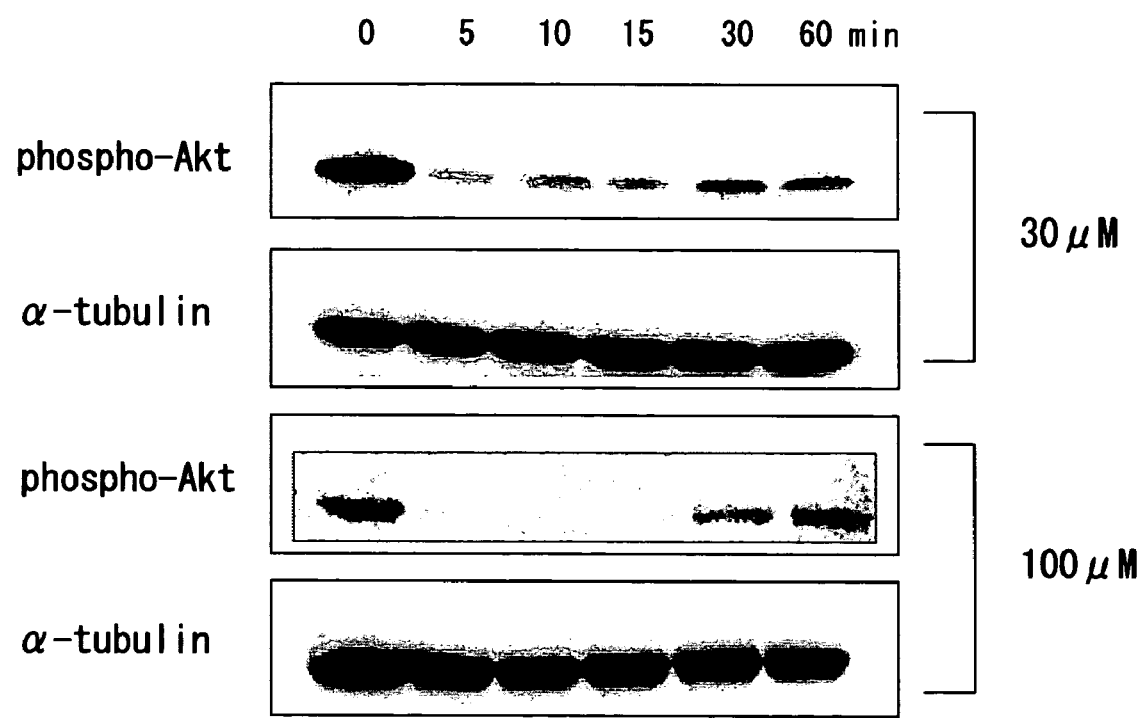
FIG. 4 shows changes with time in Akt activity in CaCo-2 cells stimulated with N-(3-oxododecanoyl)-L-homoserine lactone.
Figure 5:
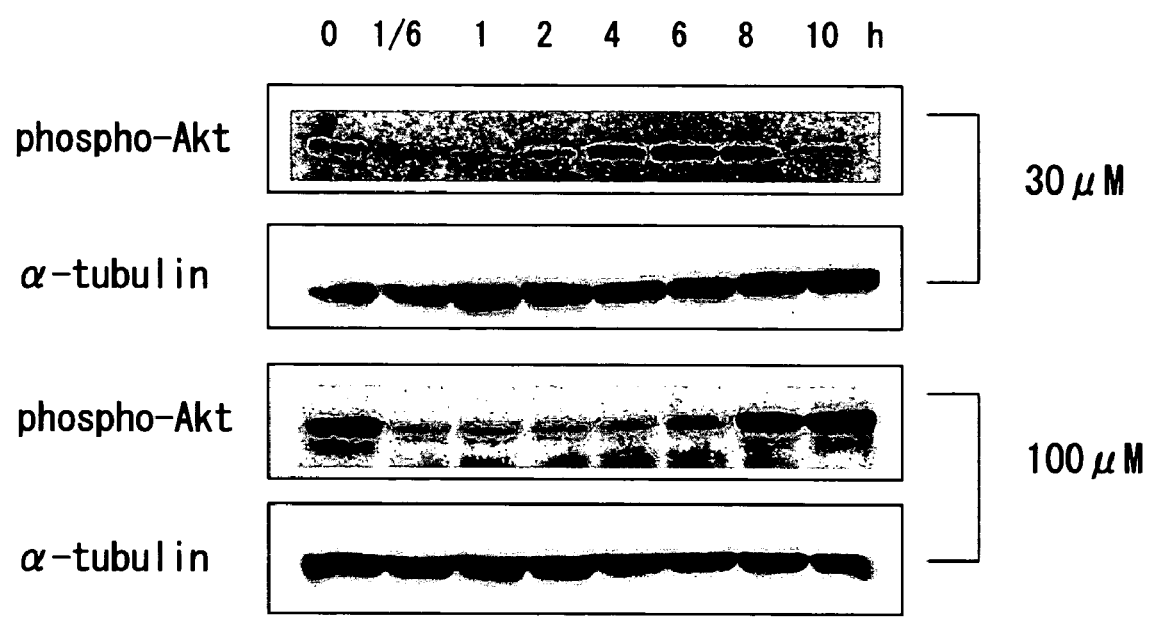
FIG. 5 shows changes with time in Akt activity in CaCo-2 cells stimulated with N-(3-oxododecanoyl)-L-homoserine lactone.

(3) Changes with Time in Akt Activity in CaCo-2 Cells Stimulated with N-(3-oxododecanoyl)-L-homoserine lactone After cell culture, N-(3-oxododecanoyl)-L-homoserine lactones with final concentrations of 30 μM and 100 μM were each added. For each case, Akt activity was measured by Western blot in a manner similar to that in (1), except for carrying out stimulation with acylated homoserine lactone in a short time course of 0, 5, 10, 30 and 60 minutes (FIG. 4), and in a long time course of 0, 10 minutes, 60 minutes, 2 hours, 4 hours, 6 hours, 8 hours and 10 hours (FIG. 5). In the case of stimulation at 30 μM, the inhibition of Akt activity peaked at 5 minutes, and lasted until 60 minutes after stimulation, and then returned to the base level within 2 hours. On the other hand, in the case of stimulation at 10 μM, the inhibition of Akt activity peaked at 5 minutes and lasted until 6 hours after stimulation.

(4) Changes in Akt Activity in Porcine Vascular Endothelial Cells Stimulated with N-(3-oxododecanoyl)-L-homoserine lactone Porcine vascular endothelial cells (PECs) were cultured at 37° C. in the presence of 5% $CO_2$ using a DMEM medium containing 10% FCS, 1% NEAA and 1% P/S (100 units/ml penicillin and 100 μg/ml streptomycin).

Figure 6:
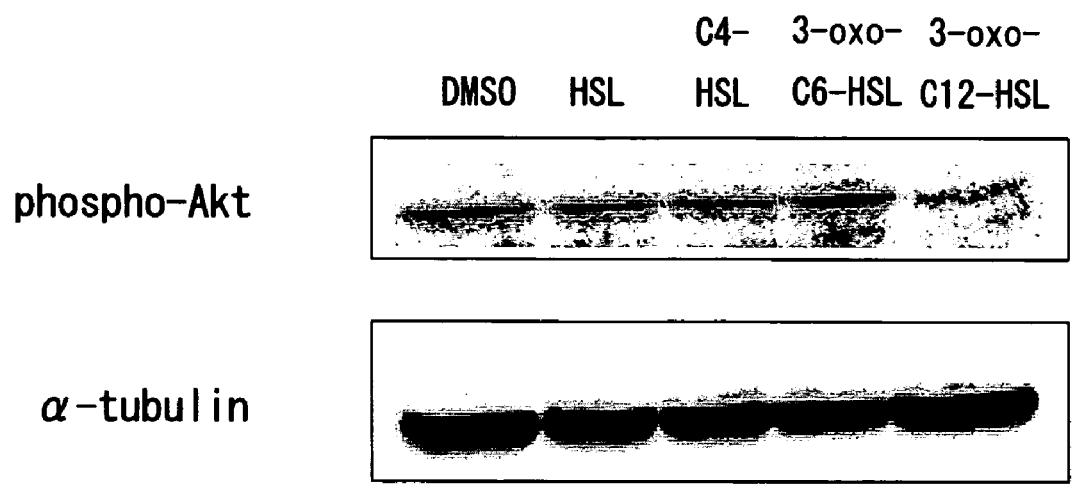
FIG. 6 shows changes in Akt activity in porcine vascular endothelial cells stimulated with DMSO, homoserine lactone hydrochloride, N-butyryl-L-homoserine lactone, N-(3-oxohexanoyl)-L-homoserine lactone and N-(3-oxododecanoyl)-L-homoserine lactone.

$6 \times 10^5$ PECs were inoculated per dish using 6 cm dishes (NUNC), washed twice with phosphate buffered saline (PBS) (-), and then cultured for 24 hours in a serum-free DMEM medium containing 1% NEAA. Subsequently, at a final concentration of 100 μM, homoserine lactone hydrochloride, N-butyryl-L-homoserine lactone, N-(3-oxohexanoyl)-L-homoserine lactone and N-(3-oxododecanoyl)-L-homoserine lactone were each added, and then each solution was allowed to react for 10 minutes. Similarly to (1), the effect of acylated homoserine lactone on Akt activity in PECs were examined by Western blotting. FIG. 6 shows the results.

The result of Western blotting revealed that N-(3-oxododecanoyl)-L-homoserine lactone significantly decreases Akt activity in PECs.

The above results suggest that specific acylated homoserine lactones induce apoptosis in PECs.

EXAMPLE 2

Analysis of MAP Kinase Activity and Akt Activity by Western Blot (1) Changes in MAP Kinase Activity and Akt Activity in CaCo-2 Cells Stimulated with N-(3-oxododecanoyl)-L-homoserine lactone A CaCo-2 carcinoma cell line of human colon cancer was purchased from American Type Culture Collection (ATCC), and cultured at 37° C. in the presence of 5% $CO_2$ using a DMEM medium containing 10% FCS, 1% NEAA and 1% P/S (100 units/ml penicillin and 100 μg/ml streptomycin).

$6 \times 10^5$ CaCo-2 cells were inoculated per dish using 6 cm dishes (NUNC), washed twice with phosphate buffered saline (PBS) (-), and then cultured in a serum-free DMEM medium containing 1% NEAA for 24 hours. Subsequently, at a final concentration of 100 μM, homoserine lactone hydrochloride and N-(3-oxododecanoyl)-L-homoserine lactone were each added, and then each solution was allowed to react for 10 minutes. Furthermore, purified acylated homoserine lactone used herein had been dissolved in DMSO in a concentration 400 times higher than the target final concentration, and then subjected to filter sterilization (φ 0.22 μm). As a control, DMSO with a final concentration of 0.25% was used. In addition, α-tubulin was used as an internal standard.

Figure 7:
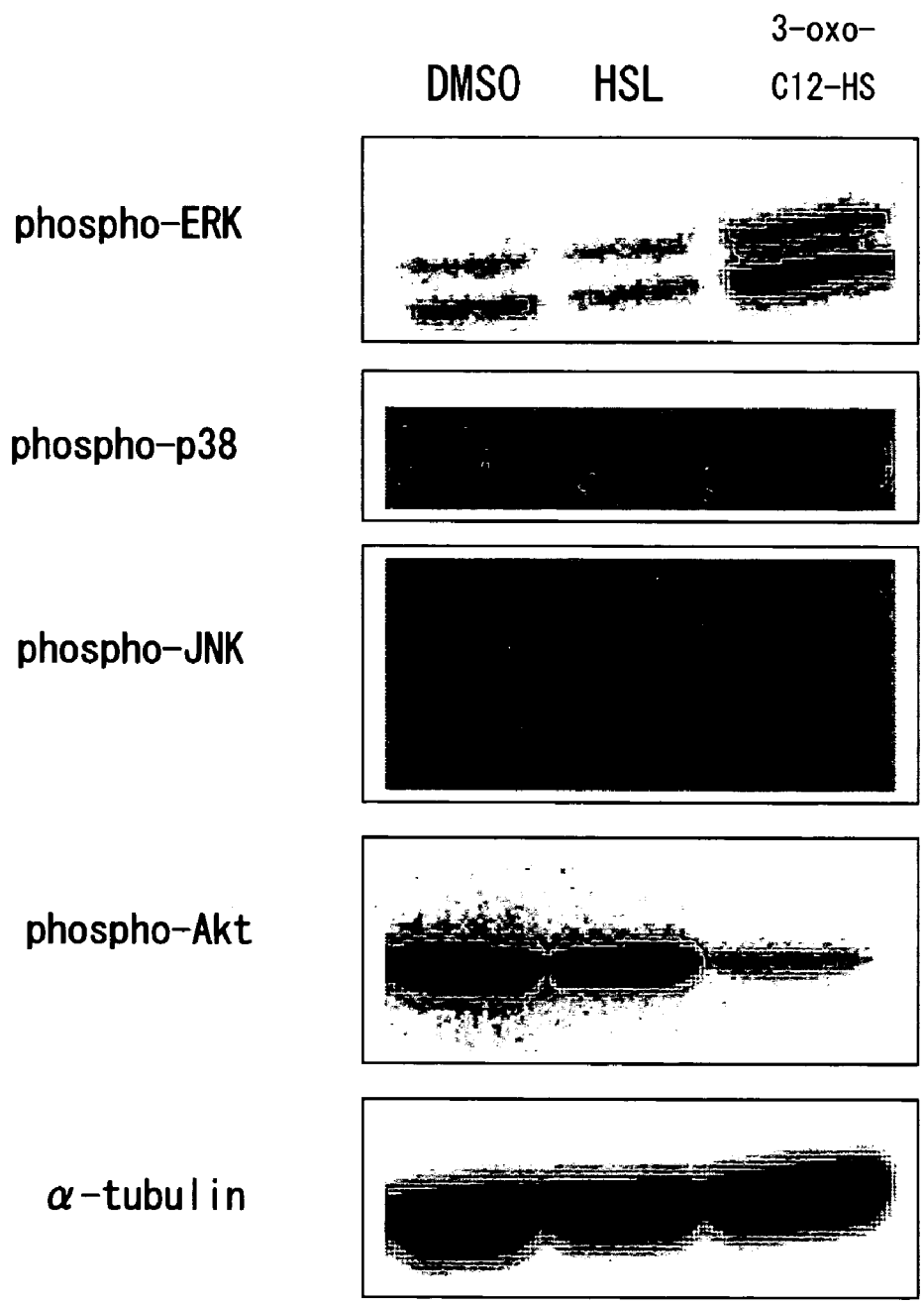
FIG. 7 shows changes in MAP kinase activity and Akt activity in CaCo-2 cells stimulated with DMSO, homoserine lactone hydrochloride and N-(3-oxododecanoyl)-L-homoserine lactone.

After reaction, the product was washed twice with cold PBS (-), and then frozen at -80° C. The cells were thawed on ice. 200 μl of a lysis buffer (50 mM HEPES, pH 7.5, 50 mM NaCl, 1 mM EDTA, 1.5 mM $MgCl_2$, 1% Triton X-100, 10% glycerin, 10 mM sodium pyrophosphate, 1 mM $Na_3VO_4$, 100 mM NaF, 1 mM PMSF, 10 μg/ml aprotinin and 10 μg/ml leupeptin) was added to the cells, and then the cells were scraped off using a scraper. The cells were allowed to stand on ice for 20 minutes, and then centrifuged at 14000 rpm at 4° C. for 15 minutes, thereby collecting the supernatant. Concentration of the collected protein was measured, and then the protein equivalent to 50 μg was subjected to SDS-PAGE. After electrophoresis, the product was blotted on a PVDF membrane. When phosphorylated ERK, JNK, p38 and Akt were measured, blocking was carried out with 0.1% Tween 20 (TBS-T) containing 5% skim milk/Tris-buffered saline. As primary antibodies, an anti-phospho-p44/42 MAP kinase antibody, an anti-phospho-SAPK/JNK antibody, an anti-phospho-p38 MAP kinase antibody, and an anti-phospho-Akt (Ser437) antibody were each used. As a secondary antibody, an HRP-labeled anti-rabbit IgG antibody was used. For the α-tubulin used as an internal standard, blocking was carried out with 5% bovine serum albumin (BSA)/TBS-T, and an anti-α-tubulin (Ab-1) antibody and an HRP-labeled anti-mouse IgG antibody were used as a primary antibody and a secondary antibody, respectively. For band detection, Renaissance™ Western Blot Chemiluminescence 255861 Reagent Plus (NEN) or Western Blotting Luminol Reagent (SANTA CRUZ BIOTECHNOLOGY) was used. FIG. 7 shows the results.

Regarding MAP kinase activity, activations of ERK, p38 and JNK were promoted only when N-(3-oxododecanoyl)-L-homoserine lactone was added. On the other hand, in CaCo-2 cells, Akt is normally in a phosphorylated (activated) form. However, the level of phosphorylated Akt significantly decreased by N-(3-oxododecanoyl)-L-homoserine lactone.

The above results revealed that acylated homoserine lactone promotes the activations of ERK, p38 and JNK, while inhibiting the activity of Akt.

Figure 8:
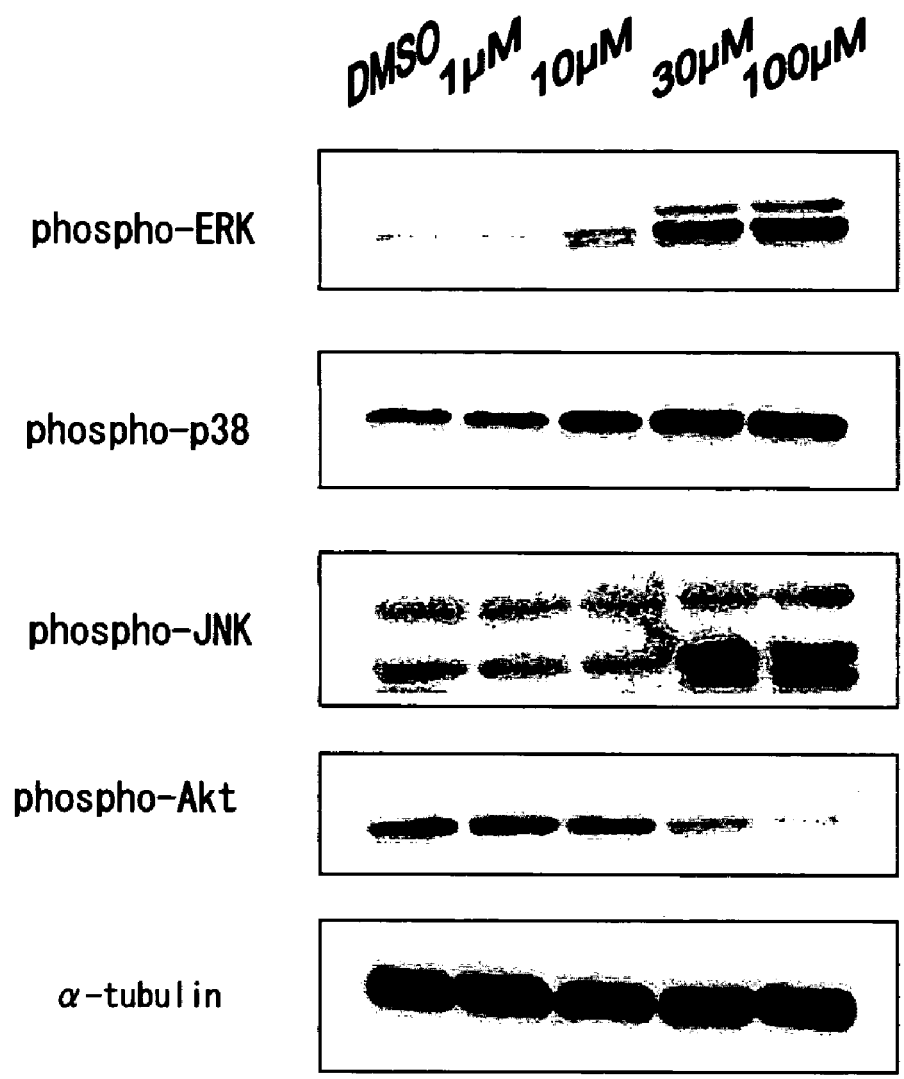
FIG. 8 shows N-(3-oxododecanoyl)-L-homoserine lactone concentration-dependent changes in MAP kinase and Akt activity in CaCo-2 cells.

(2) N-(3-oxododecanoyl)-L-homoserine-lactone Concentration-dependent Changes in MAP Kinase Activity and Akt Activity in CaCo-2 Cells After cell culture, MAP kinase activity and Akt activity were analyzed by Western blot in a manner similar to that used in (1), except that N-(3-oxododecanoyl)-L-homoserine lactones in final concentrations of 0 μM (0.25% DMSO), 1 μM, 10 μM, 30 μM and 100 μM were each added and each solution was allowed to react for 10 minutes (FIG. 8).

Figure 9:
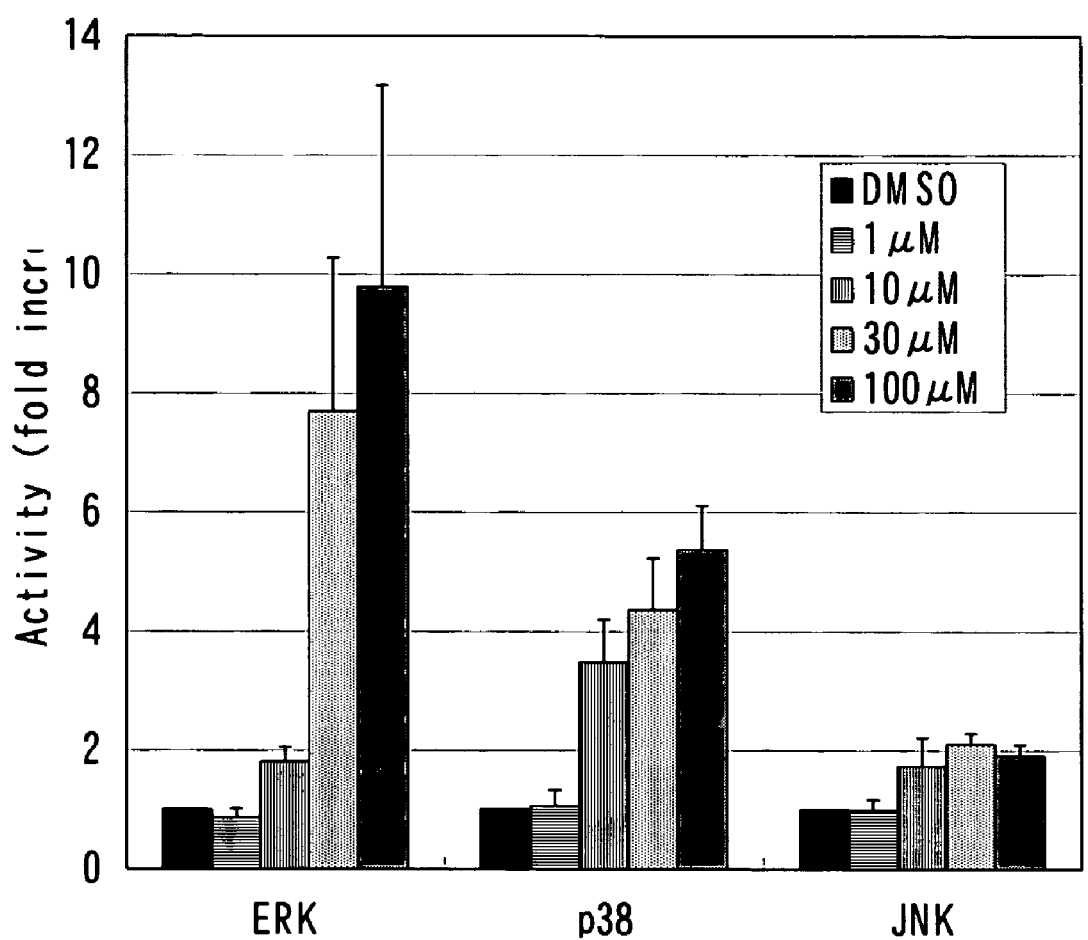
FIG. 9 shows the results of quantifying the band intensities of MAP kinase in FIG. 8 by LAS-1000 and converting the results into numerical data.
Figure 10:
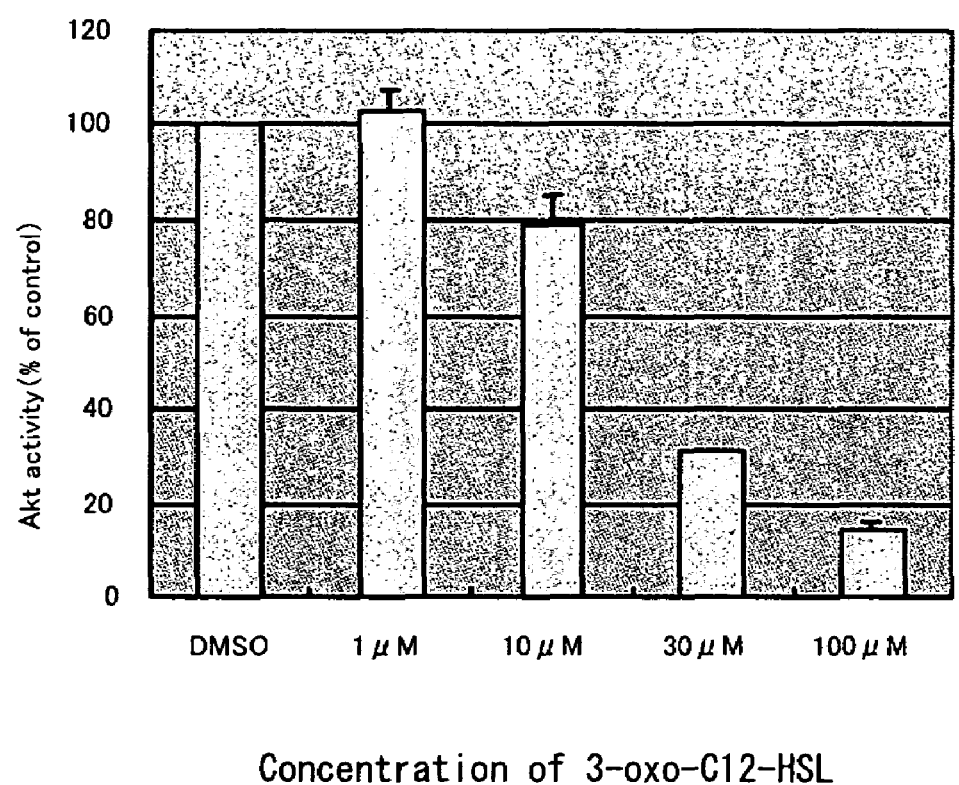
FIG. 10 shows the results of quantifying the band intensities of Akt in FIG. 8 by LAS-1000 and converting the results into numerical data.

The results of quantifying the band intensities in FIG. 8 by LAS-1000 and converting the results into numerical data are each shown in FIGS. 9 and 10. At concentrations of 10 μM or more, the levels of phosphorylated ERK and p38 significantly increased. At concentrations of 10 μM, 30 μM and 100 μM, ERK activity increased 1.5, 7.7 and 9.8 times, respectively, and p38 activity increased 3.2, 4.4 and 5.4 times, respectively. For JNK activity, no concentration-dependent significant difference was observed. Also, the inhibition of Akt activity similarly began at 10 µM. At 10 µM, 30 µM and 100 µM, Akt activity decreased to 79%, 31% and 14%, respectively, of that in a case where no stimulation was provided.

The above results showed that in CaCo-2 cells, 10 µM or more acylated homoserine lactone significantly inhibits Akt activity. Moreover, it was also shown that 10 µM or more acylated homoserine lactone activates ERK, p38 and JNK.

Figure 11:
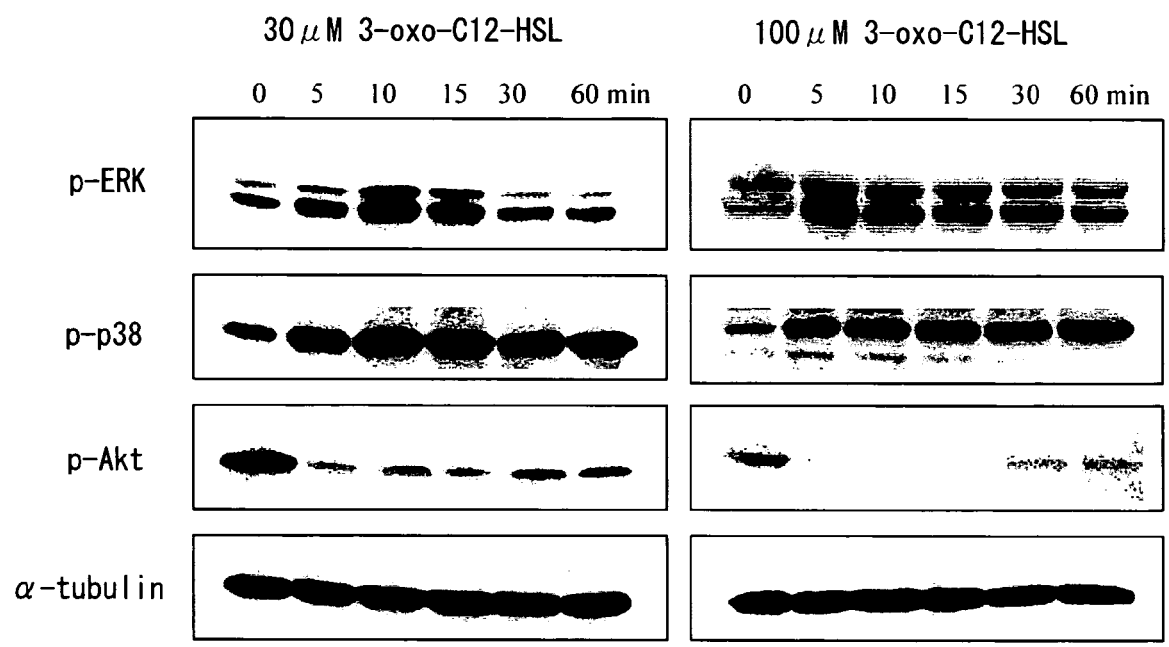
FIG. 11 shows changes with time in MAP kinase activity and Akt activity in CaCo-2 cells stimulated with N-($^3$-oxododecanoyl)-L-homoserine lactone.
Figure 12:
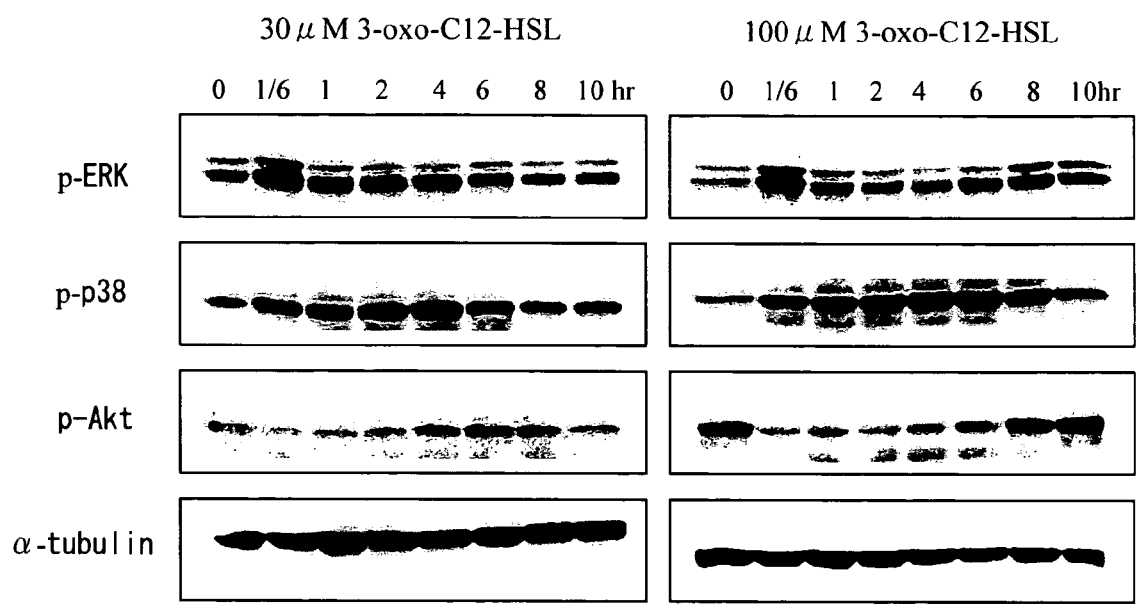
FIG. 12 shows changes with time in MAP kinase activity and Akt activity in CaCo-2 cells stimulated with N-(3-oxododecanoyl)-L-homoserine lactone.

(3) Changes with Time in MAP Kinase Activity and Akt Activity in CaCo-2 Cells Stimulated with N-(3-oxododecanoyl)-L-homoserine lactone After cell culture, N-(3-oxododecanoyl)-L-homoserine lactone with final concentrations of 30 µM and 100 µM were added. For each case, MAP kinase activity and Akt activity were measured by Western blot in a manner similar to that in (1), except for carrying out stimulation with acylated homoserine lactone in a short time course of 0, 5, 10, 30 and 60 minutes (FIG. 11), and in a long time course of 0, 10 minutes, 60 minutes, 2 hours, 4 hours, 6 hours, 8 hours and 10 hours (FIG. 12). In the case of stimulation at 30 µM, both ERK and p38 activities increased with a peak at 10 minutes. However, while ERK activity returned to the base level within 30 minutes, p38 activity lasted until 4 hours after stimulation. The inhibition of Akt activity in the case of stimulation at 30 µM peaked at 5 minutes and lasted until 60 minutes after stimulation, and returned to the base level within 2 hours. ERK activation took place with two steps in the case of stimulation at 100 µM. Specifically, in the first step, ERK activity peaked at 5 minutes and returned to the base level within 2 hours, and in the second step, ERK activity began to increase at 4 hours, peaked at 8 hours, and returned to the base level within 10 hours. The ERK activation in the second step is thought to take place after DNA had been damaged. On the other hand, p38 activation in the case of stimulation at 100 µM peaked at 5 minutes, and p38 activity lasted until 8 hours after stimulation. The inhibition of Akt activity peaked at 5 minutes and lasted until 6 hours after stimulation.

EXAMPLE 3

Evaluation of Viability by Trypan Blue Staining $2\times10^5$ CaCo-2 cells were inoculated in a 3.5 cm dish (NUNC), washed twice with PBS (-), and then cultured in a serum-free DMEM medium containing 1% NEAA for 24 hours. Various agents [N-(3-oxododecanoyl)-L-homoserine lactones with final concentrations between 1 and 100 µM] were added, followed by 12 hours of culture. 0.25% DMSO was used as a control. Subsequently, the supernatant and the cells removed from the dish using trypsin-EDTA (TE) were centrifuged at 800 rpm at room temperature for 5 minutes. The supernatant was removed, and then dilution was carried out with 200 µl of DMEM. 50 µl of the dilution was taken in an Eppen tube, an equivalent volume of Trypan blue stain was added, and then the cell count was measured using a hemacytometer. At this time, the sum of the dead cell count and the viable cell count to be measured was determined to be 200 cells or more.

Figure 13:
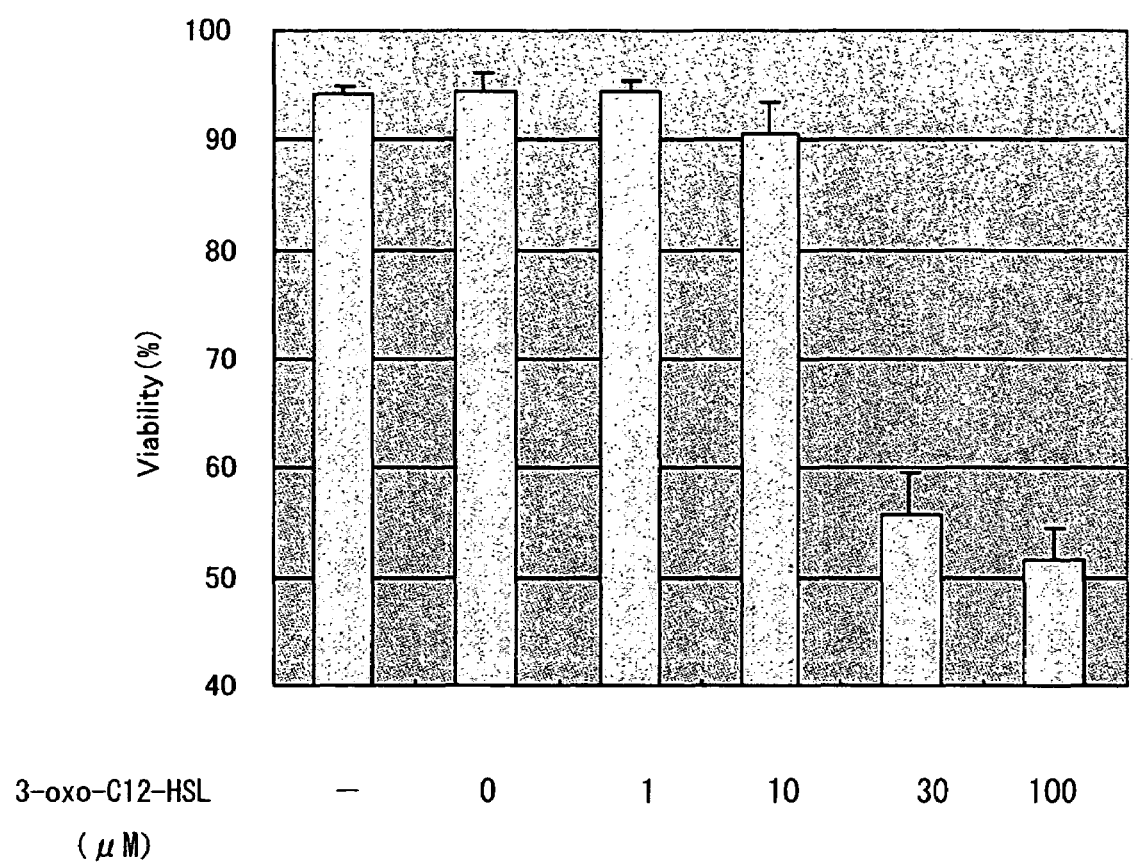
FIG. 13 shows the results of evaluating cell viability in the presence of acylated homoserine lactone by Trypan blue staining.

A significant decrease was observed in viability in a manner depending on the concentration of N-(3-oxododecanoyl)-L-homoserine lactone. With 10 µM, 30 µM and 100 µM N-(3-oxododecanoyl)-L-homoserine lactones, the viabilities respectively decreased to 90%, 55% and 51% (FIG. 13). These results showing that the viability was significantly decreased at concentrations of 30 µM or more, are consistent with the results showing that increased MAP kinase activity and the inhibition of Akt activity were significantly observed in Western blot analysis at around 30 µM. Moreover, the viabilities in the case of adding 0.25% DMSO were both 94%. Thus, it is considered that since stimulation with 1 µM N-(3-oxododecanoyl)-L-homoserine lactone resulted in a viability of 94%, the effect of DMSO on viability can be ignored.

EXAMPLE 4

Observation of Chromatin Condensation and Determination of Apoptosis by Hoechst33342 Staining To determine whether the cell death of CaCo-2 observed in Examples 1 and 2 were due to apoptosis or necrosis, morphological evaluation was carried out using Hoechst33342 fluorescent dye for chromatin staining.

$2\times10^4$ CaCo-2 cells were inoculated on an 8-well culture slide (Collagen I Cellware BioCoat, Becton Dickinson), washed twice with PBS (-), and then cultured in a serum-free DMEM medium containing 1% NEAA for 24 hours. 3-oxododecanoyl homoserine lactone was added at each concentration (1 to 100 µM). After 12 hours of culture, the cells were fixed by 4% paraformaldehyde-3% sucrose/PBS, chromatin staining was carried out using Hoechst 33342 fluorescent dye, and then the cells were observed under a fluorescence microscope. With a magnification of ×400, 5 visual fields were selected at random. Apoptotic cells and normal cells were counted and the proportion of apoptotic cells was calculated. These steps were denoted as n=1, and conducted 3 times or more.

Figure 14:
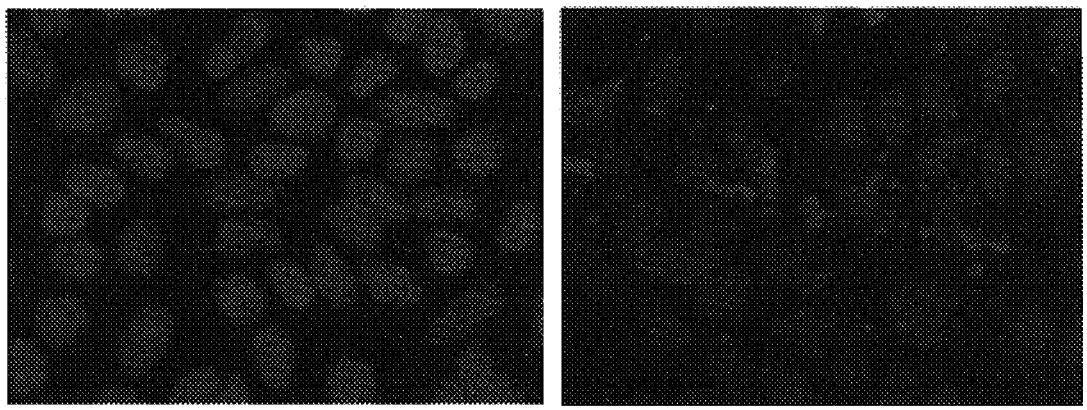
FIG. 14 shows the results of determining apoptosis in cells in the presence of acylated homoserine lactone by chromatin condensation using Hoechst 33342 staining.
Figure 15:
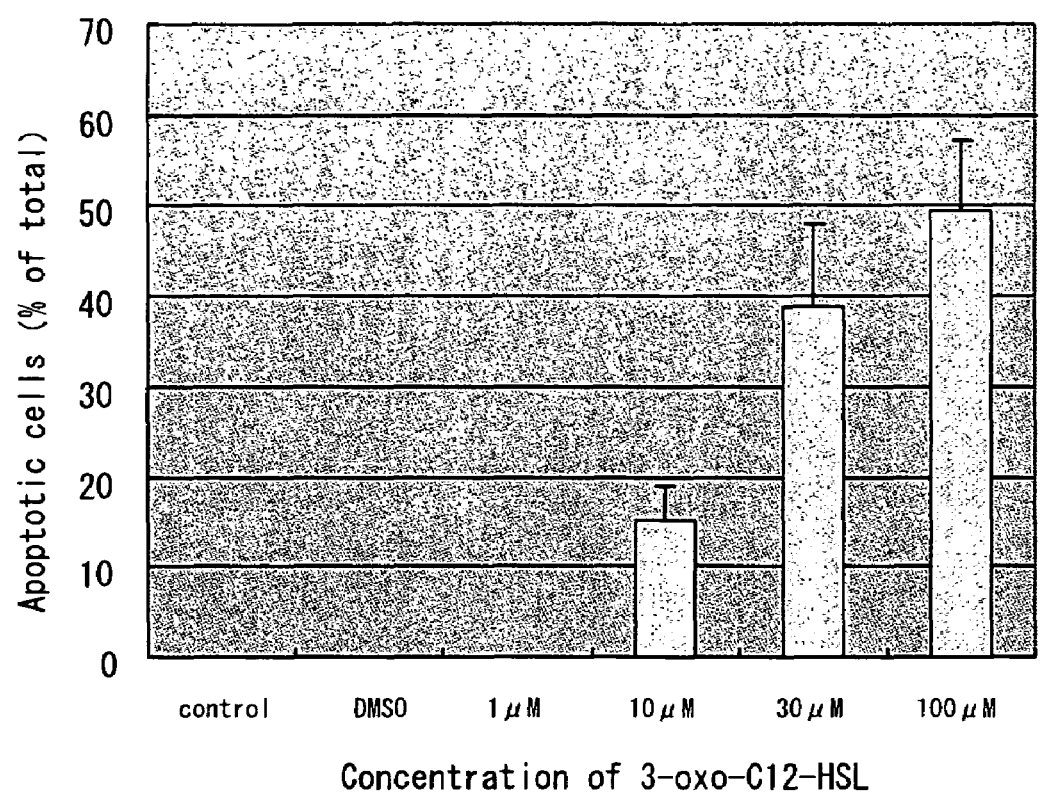
FIG. 15 shows the results of quantifying apoptosis by counting apoptotic cells for which chromatin condensation was observed.

The apoptotic cells exhibiting chromatin condensation were observed at concentrations of 10 µM or more of N-(3-oxododecanoyl)-L-homoserine lactone. However, in the cases of 0.25% DMSO and 1 µM N-(3-oxododecanoyl)-L-homoserine lactone, only normal cells were observed (FIG. 14). FIG. 15 shows the result of quantifying apoptosis by counting apoptotic cells in which chromatin condensation was observed. The proportions of apoptotic cells to the total cell count were 15%, 39% and 50% respectively in the cases of 10 µM, 30 µM and 100 µM N-(3-oxododecanoyl)-L-homoserine lactones. These values are also consistent with the decreases in viabilities. Therefore, it was determined that cell death of CaCo-2 resulting from N-(3-oxododecanoyl)-L-homoserine lactone was due to apoptosis.

EXAMPLE 5

Evaluation of Apoptosis by DNA Fragmentation

In another method for determining whether the cell death of CaCo-2 observed in Examples 1 and 2 was due to apoptosis or necrosis, DNA fragmentation was evaluated.

$5\times10^6$ CaCo-2 cells were inoculated per 15 cm dish (NUNC), washed twice with PBS (-), and then cultured in a serum-free DMEM medium containing 1% NEAA for 24 hours. N-(3-oxododecanoyl)-L-homoserine lactone was added at each concentration (1 µM to 100 µM), followed by 12 hours of culture. Subsequently, the supernatant and the cells removed from the dish using TE were centrifuged at room temperature at 800 rpm for 5 minutes, and the supernatant was removed. The cells were suspended with 300 µl of PBS (-), and then the suspension was centrifuged again at 4° C. at 2500 rpm for 5 minutes, and the supernatant was removed. The cells were lysed by the addition of 300 µl of a cytolysis buffer [10 mM Tris-HCl (pH 7.4), 10 mM EDTA (pH 8.0), 0.5% Triton X-100], and then allowed to stand on ice for 10 minutes, thereby extracting DNA fragments. The extract was centrifuged at 4° C. at 14000 rpm for 10 minutes. RNase A was added to the obtained supernatant, and then incubation was carried out at 37° C. for 1 hour. Proteinase K was further added, and then incubation was carried out at 50° C. for 30 minutes. The extract of the DNA fragments was concentrated by ethanol precipitation, and then electrophoresis was carried out using 2% agarose gel. After the gel was stained with ethidium bromide, DNA fragmentation was detected under a UV transilluminator.

Figure 16:
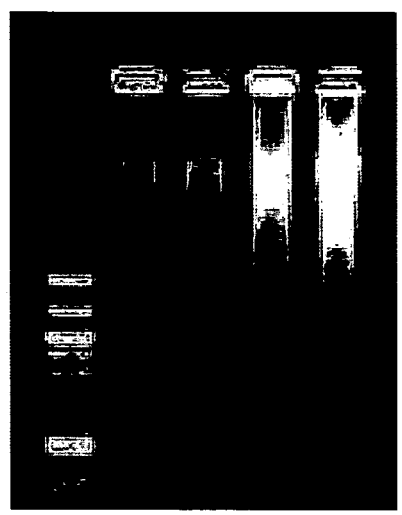
FIG. 16 shows the results of evaluating DNA fragmentation in order to determine whether the death of CaCo-2 cells was due to apoptosis or necrosis.

When the detection of a DNA ladder was conducted for CaCo-2 cells cultured for 12 hours in the presence of each of 0 μM, 1 μM, 10 μM, 30 μM and 100 μM N-(3-oxododecanoyl)-L-homoserine lactones, the DNA ladder was observed at the concentrations of 30 μM or more (FIG. 16).

From the results, it is also considered that screening is preferably carried out at concentrations of 30 μM or more of acylated homoserine lactones in the case of using CaCo-2 cells.

EXAMPLE 6

Measurement of Caspase Activity

The activities of caspase (caspase-3 and caspase-9) and PARP (poly-ADP ribose polymerase) were measured in a manner similar to those in Examples 1 and 2 by Western blot analysis using each of anti-activated (cleaved) caspase antibodies, that is, an anti-cleaved caspase-3 antibody, an anti-cleaved caspase-9 antibody (D330) and an anti-cleaved PARP antibody (D214).

Figure 17:
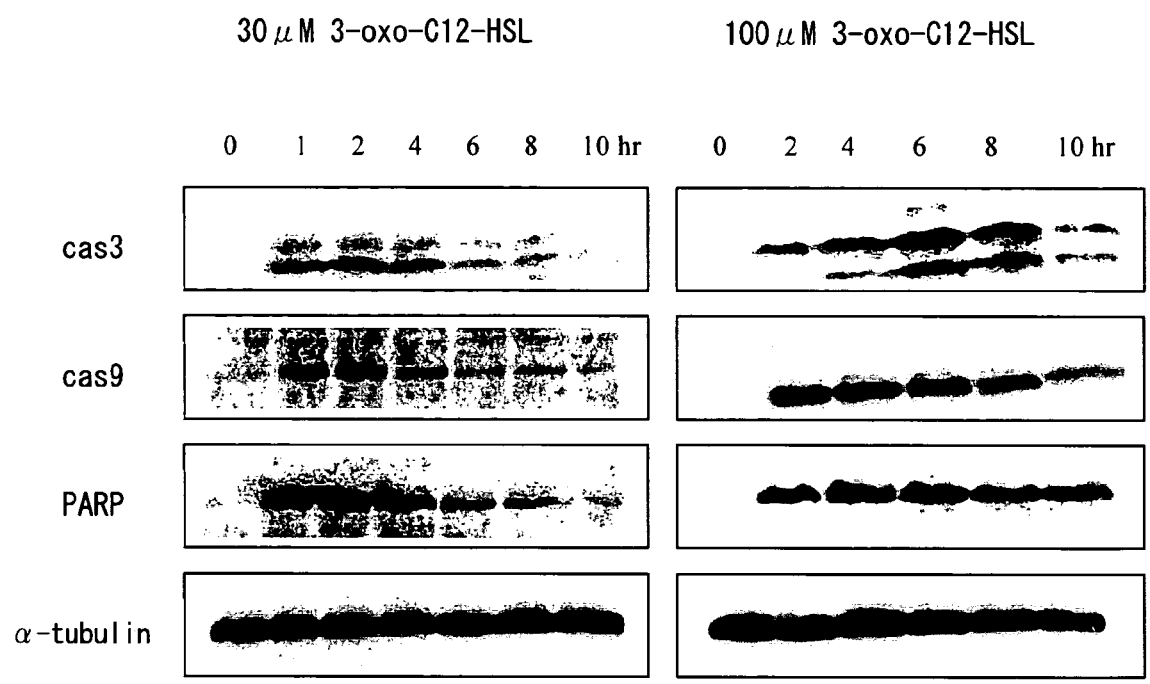
FIG. 17 shows the results of measuring the culture-time dependency of caspase activity in the presence of acylated homoserine lactone by Western blot.

N-(3-oxododecanoyl)-L-homoserine lactones with final concentrations of 30 μM and 100 μM were each added to cultured CaCo-2 cells. Caspase-3, caspase-9 and PARP activities were analyzed over time by Western blot at 0 hours, 1 hour, 2 hours, 4 hours, 6 hours, 8 hours and 10 hours after culture. FIG. 17 shows the result. Whereas at 30 μM, activated caspase-3 began to be detected 1 hour after stimulation and the activity lasted until 4 hours after stimulation, at 100 μM the activity peaked at 6 hours and lasted until 10 hours after stimulation. Cleaved caspase-9 and cleaved PARP were detected by reprobing each membrane. Whereas caspase-9 activity was observed to be strong at 1, 2 and 4 hours and its weak activity lasted until 8 hours after stimulation at 30 μM, its strong activity lasted until 8 hours after stimulation at 100 μM. Regarding cleaved PARP, it also showed behavior similar to that of cleaved caspase-9.

Figure 18:
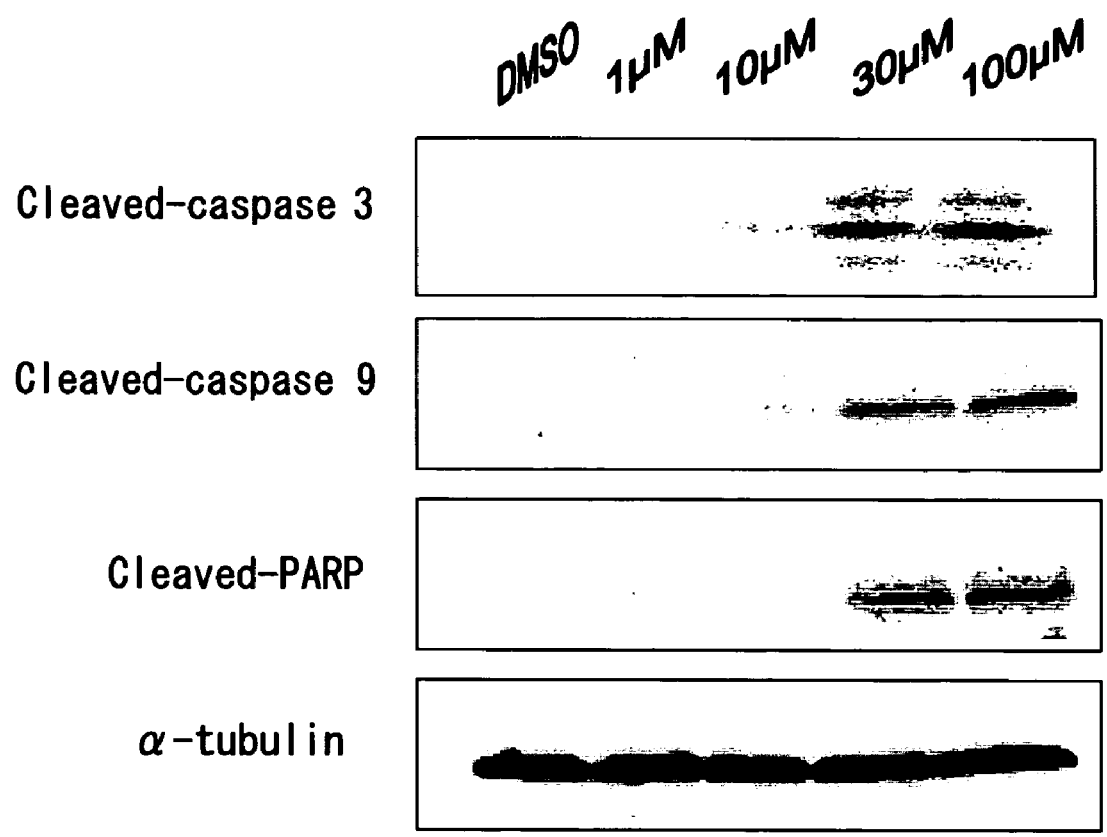
FIG. 18 shows the results of measuring the acylated homoserine lactone concentration dependency of caspase activity by Western blot.

Next, 3 hours of reaction with N-(3-oxododecanoyl)-L-homoserine lactone was carried out at concentrations of 0, 1, 10, 30, and 100 μM, and then caspase and PARP activities were measured. As shown in FIG. 18, only at concentrations of 30 μM and 100 μM, cleaved caspase and cleaved PARP were detected. These results were also consistent with the result obtained by Western blot analysis showing that the activation of MAP kinase, the inhibition of Akt activity, decreased viabilities and the appearance of apoptotic cells significantly occurred at 30 μM or more.

EXAMPLE 7

Figure 19:
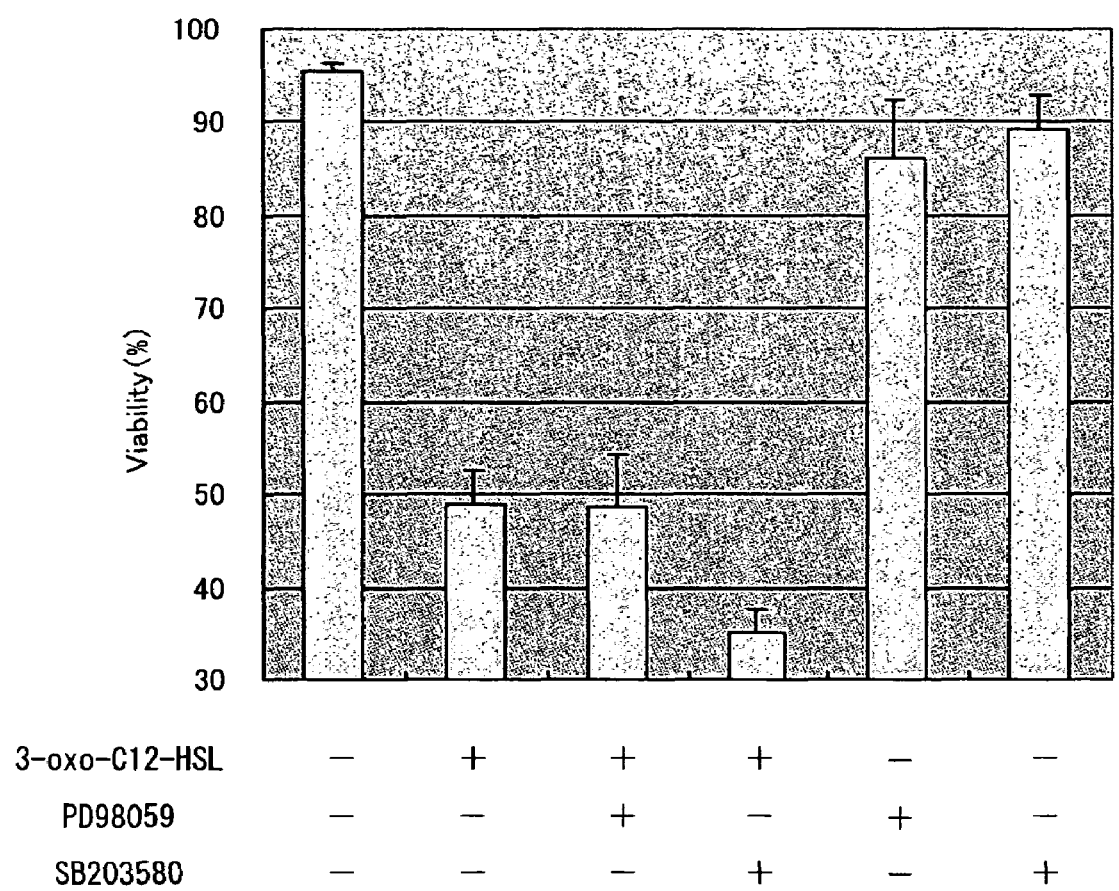
FIG. 19 shows the effects of various kinase inhibitors (PD98059 and SB203580) on acylated homoserine lactone-dependent apoptosis in CaCo-2 cells.

N-(3-oxododecanoyl)-L-homoserine-lactone-dependent Effects of Various Kinase Inhibitors (PD98059 and SB203580) on Apoptosis in CaCo-2 Cells $2\times10^5$ CaCo-2 cells were inoculated per 3.5 cm dish, cultured for 12 hours in the presence of 10% serum, washed twice with PBS (-), and then synchronously cultured in a serum-free medium for 24 hours. Pretreatment with various inhibitors (50 μM PD98059 and 20 μM SB203580) or DMSO was carried out for 30 minutes. Then 30 μM N-(3-oxododecanoyl)-L-homoserine lactone or DMSO was added, the cells were cultured for 12 hours, and then viability was measured by Trypan blue staining. FIG. 19 shows the results.

N-(3-oxododecanoyl)-L-homoserine lactone (30 μM) caused viability to decrease from 96% to 49%. The case of pretreatment with PD98059 (MEK inhibitor), the inhibitor of the ERK pathway, showed viability that was almost the same as that in a case where N-(3-oxododecanoyl)-L-homoserine lactone had been added alone. That is, no effect by pretreatment with PD98059 on viability was observed. On the other hand, in a case of pretreatment with SB203580, the p38 activity inhibitor, viability further decreased to 35%.

Based on the above results, it can be said that no pathways of ERK or p38 are involved in N-(3-oxododecanoyl)-L-homoserine lactone-dependent decreases in viability. Furthermore, regarding p38, it was suggested that p38 indeed functions as a signal opposed to the negative factor, N-(3-oxododecanoyl)-L-homoserine lactone which induces apoptosis.

All publications, patents and patent applications cited herein are incorporated herein by reference in their entirety.

What is claimed is:

1. A method of screening for a substance that inhibits acylated homoserine lactone, comprising
    (i) culturing animal cells with a test substance in the presence of acylated homoserine lactone represented by formula I:

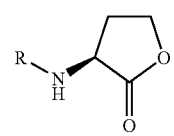

(I)

wherein R is $C_{4-30}$ linear or branched acyl, which may be substituted; and
    (ii) detecting phosphorylated-Akt, wherein increased phosphorylation reflects inhibition of acylated homoserine lactone; and
    (iii) identifying the substance as one that inhibits acylated homoserine lactone.

2. A kit for using in the screening method of claim 1, comprising the following elements:
    a) an acylated homoserine lactone represented by formula I:

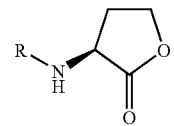

(I)

wherein R is as defined above,
    b) an animal cell, and
    c) an anti-phosphorylated Akt antibody.

* * * * *